(12) United States Patent
Sato et al.

(10) Patent No.: US 10,792,195 B2
(45) Date of Patent: Oct. 6, 2020

(54) POWDER SUPPLY METHOD, METHOD FOR MANUFACTURING POWDER-CONTAINING ARTICLE USING SAME, POWDER SUPPLY DEVICE, AND DEVICE FOR MANUFACTURING POWDER-CONTAINING ARTICLE USING SAME

(71) Applicant: ZUIKO CORPORATION, Osaka (JP)

(72) Inventors: Hitoshi Sato, Osaka (JP); Hideyuki Nakamura, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 132 days.

(21) Appl. No.: 16/073,047

(22) PCT Filed: Jan. 25, 2017

(86) PCT No.: PCT/JP2017/002522
§ 371 (c)(1),
(2) Date: Jul. 26, 2018

(87) PCT Pub. No.: WO2017/131025
PCT Pub. Date: Aug. 3, 2017

(65) Prior Publication Data
US 2019/0029889 A1    Jan. 31, 2019

(30) Foreign Application Priority Data

Jan. 27, 2016   (JP) ................... 2016-013156

(51) Int. Cl.
*A61F 13/15*   (2006.01)
*B05C 11/10*   (2006.01)
(Continued)

(52) U.S. Cl.
CPC ........ *A61F 13/15617* (2013.01); *A61F 13/15* (2013.01); *B05C 5/0225* (2013.01);
(Continued)

(58) Field of Classification Search
CPC ..... B05C 5/00; B05C 5/0225; B05C 11/1026; F16K 3/02; F16K 31/44
See application file for complete search history.

(56) References Cited

U.S. PATENT DOCUMENTS

| 2,749,940 A | 6/1956 | Bronson, II |
| 4,861,405 A | 8/1989 | Kassai |

(Continued)

FOREIGN PATENT DOCUMENTS

| CN | 1056109 | 11/1991 |
| CN | 1089465 | 7/1994 |

(Continued)

OTHER PUBLICATIONS

Extended European Search Report dated Oct. 9, 2018 in European Patent Application No. 17744255.5.

(Continued)

*Primary Examiner* — Alexander M Weddle
(74) *Attorney, Agent, or Firm* — Wenderoth, Lind & Ponack, L.L.P.

(57) ABSTRACT

A method includes distributing a powder onto a first sheet, periodically closing a distribution port by a first opening-closing portion, and periodically closing the distribution port by a second opening-closing portion in the same cycle period as that of the first opening-closing portion and at a timing later than that of the first opening-closing portion. The method also includes moving the second opening-closing portion such that it extends from an upstream-side edge of the first opening-closing portion toward an upstream side of a movement direction, during a time period during which the upstream-side edge of the first opening-closing portion overlaps the distribution port. Further, the method (Continued)

includes setting a difference between timings at which the first and second opening-closing portion overlap the distribution port, respectively.

8 Claims, 16 Drawing Sheets

(51) Int. Cl.
    *B05C 5/02*     (2006.01)
    *F16K 31/44*     (2006.01)
    *F16K 3/02*     (2006.01)
    *B05C 5/00*     (2006.01)
    *A61F 13/539*     (2006.01)

(52) U.S. Cl.
    CPC ............ *B05C 11/1026* (2013.01); *F16K 3/02* (2013.01); *F16K 31/44* (2013.01); *A61F 2013/53908* (2013.01); *B05C 5/00* (2013.01)

(56) References Cited

U.S. PATENT DOCUMENTS

| | | |
|---|---|---|
| 5,102,597 A | 4/1992 | Roe et al. |
| 5,124,188 A | 6/1992 | Roe et al. |
| 2006/0278335 A1 | 12/2006 | Moriura et al. |
| 2009/0056867 A1 | 3/2009 | Moriura et al. |
| 2013/0284361 A1 | 10/2013 | Tsujimoto et al. |
| 2015/0351973 A1* | 12/2015 | Tsujimoto ......... A61F 13/15617 222/1 |
| 2015/0352824 A1 | 12/2015 | Tsujimoto et al. |
| 2016/0056493 A1 | 2/2016 | Umeda et al. |

FOREIGN PATENT DOCUMENTS

| | | | |
|---|---|---|---|
| JP | 60-77910 | 5/1985 | |
| WO | 86/00829 | 2/1986 | |
| WO | 94/07547 | 4/1994 | |
| WO | 2005/011548 | 2/2005 | |
| WO | 2012/108331 | 8/2012 | |
| WO | 2014/104115 | 7/2014 | |
| WO | 2014/104118 | 7/2014 | |
| WO | WO-2014104118 A1 * | 7/2014 | ......... A61F 13/5323 |
| WO | 2014/155168 | 10/2014 | |

OTHER PUBLICATIONS

Office Action dated Mar. 7, 2019 in corresponding Chinese Patent Application No. 20178000831.0.X with partial English translation.
International Search Report dated Apr. 18, 2017 in International (PCT) Application No. PCT/JP2017/002522.

* cited by examiner

POWDER SUPPLY METHOD, METHOD FOR MANUFACTURING POWDER-CONTAINING ARTICLE USING SAME, POWDER SUPPLY DEVICE, AND DEVICE FOR MANUFACTURING POWDER-CONTAINING ARTICLE USING SAME

TECHNICAL FIELD

The present invention relates a method and device for supplying a powder to a sheet, and a method and apparatus for manufacturing a powder-containing article containing a powder, using them.

BACKGROUND ART

Heretofore, a powder-containing article containing a powder, formed by supplying the powder to a sheet, has been used in some cases. For example, there has been a case where a powder-containing article containing a liquid-absorbable powder is used for an absorbent body in a disposable diaper.

As an example of a method for supplying a powder to a sheet, a method described in WO 2014/104118A has been known.

In the method described in WO 2014/104118A, a powder is dropped and supplied from an outlet of a powder storage section to a first sheet being conveyed along a given conveyance path to thereby continuously manufacture a powder-containing article. Subsequently, this powder-containing article is cut into given lengths. In this case, if part of the powder is contained in a cut area, it can leak from the cut area during cutting and can damage a cutting blade. For this reason, in the method described in WO 2014/104118A, an opening-closing means is rotationally driven by a motor, and a distribution port is periodically closed by the opening-closing means, to thereby intermittently supply a powder to a surface of the first sheet. This enables cutting in a region to which no powder has been supplied.

In a powder-containing article containing a powder, there is a need to change the length of a discrete article after cutting the powder-containing article, depending on the type of a target assembly in which this powder-containing article is to be applied, or the like. On the other hand, it is desired that the length of a region having no powder (hereinafter referred to occasionally and appropriately as "blank region") is set to an arbitrary length, irrespective of a required length of the discrete article.

In this regard, in case of using the method described in WO 2014/104118A, the length of a region lying between two adjacent blank regions and holding a powder supplied thereto (this region will hereinafter be referred to occasionally and appropriately as "holding region") can be changed, for example, by changing the cycle period of the opening-closing means. In this case, however, a time period during which the opening-closing means closes the distribution port is changed along with the change in the cycle period, and therefore the length of the blank region is also undesirably changed. That is, in the method described in WO 2014/104118A, the time period during which the opening-closing means closes the distribution port and the cycle period of the opening-closing means are changed in proportional relation to each other, thereby leading to a problem that the length of the holding region and the length of the blank region cannot be changed separately. As an example of a measure against this problem, it is conceivable to prepare a plurality of types of opening-closing means having different dimensions in a direction parallel to a longitudinal direction of a sheet constituting a powder-containing article, and appropriately use one of them in an exchangeable manner. In this case, however, work of exchanging the opening-closing means is required, leading to deterioration in work efficiency.

In the method described in WO 2014/104118A, the length of the blank region can be set and changed independently, irrespective of the length of the holding region, for example, by increasing the rotational speed of the opening-closing means only during a time period during which the opening-closing means closes the distribution port, in the course of 360-degree rotation thereof (within the cycle period), as compared to the remaining time period, to thereby vary the rotational speed during 360-degree rotation of the opening-closing means. In this case, however, a load is undesirably imposed on a motor for driving the opening-closing means. Particularly, in the case where the opening-closing means is driven at high speeds, it is necessary to frequently vary the rotational speed of the opening-closing means, so that a load imposed on the motor becomes excessive.

SUMMARY OF THE INVENTION

Technical Problem

It is an object of the present invention to provide a powder supply method, a powder-containing article manufacturing method using the powder supply method, a powder supply device, and the powder-containing article manufacturing apparatus equipped with the powder supply device, each capable of changing the length of a region holding a powder and the length of a region having no powder, in a powder-containing article, respectively, to adequate values, separately and easily.

Solution to Technical Problem

As a solution to the above problem, the present invention provides a powder supply method for supplying a powder to a sheet being conveyed along a conveyance path. The powder supply method implements: a distribution step of dropping the powder from a storage section storing therein the powder, to distribute the powder onto a surface of the sheet through a distribution port; a first closing step of moving a first opening-closing portion such that the first opening-closing portion periodically overlaps the distribution port when viewed from vertically above the distribution port, to periodically close the distribution port by the first opening-closing portion; a second closing step of moving a second opening-closing portion such that the second opening-closing portion overlaps the distribution port when viewed from vertically above the distribution port, in a same cycle period as that of the first opening-closing portion and at a timing later than that of the first opening-closing portion, to periodically close the distribution port by the second opening-closing portion, and moving the second opening-closing portion such that the second opening-closing portion extends from an upstream-side edge of the first opening-closing portion lying on an upstream side of a movement direction of the first opening-closing portion toward the upstream side of the movement direction of the first opening-closing portion, during a time period during which the upstream-side edge of the first opening-closing portion overlaps the distribution port, when viewed from vertically above the distribution port; and a timing setting step of setting a difference between a timing at which the second opening-closing portion overlaps the distribution port when viewed from vertically above the distribution port, and a timing at which the first opening-closing portion overlaps the distribution port when viewed from vertically above the distribution port.

The present invention further provides a method for manufacturing a powder-containing article containing a powder, by using the above powder supply method. The method implements: the timing setting step; a conveyance step of conveying the sheet along the conveyance path; a powder supply step of supplying the powder onto a surface of the sheet being conveyed along the conveyance path; a second sheet supply step of supplying a second sheet onto the surface of the sheet being conveyed along the conveyance path, at a powder supply position where the powder is supplied to the sheet or at a position downstream of the powder supply position in the conveyance direction of the sheet; and a bonding step of bonding the sheet and the second sheet supplied onto the surface of the sheet, together, wherein the powder supply step includes implementing the distribution step, the first closing step, and the second closing step.

The present invention further provides a powder supply device for supplying a powder to a sheet being conveyed along a conveyance path. The powder supply device comprises: a storage section storing therein the powder; a distribution port which allows the powder falling from the storage section to pass therethrough toward an obverse side of the sheet; a first opening-closing portion and a second opening-closing portion each having a shape capable of closing the distribution port when viewed from vertically above the distribution port; a first drive device which drives the first opening-closing portion; a second drive device which drives the second opening-closing portion; and a control device which controls the first drive device and the second drive device, wherein: the first drive device moves the first opening-closing portion such that the first opening-closing portion periodically overlaps the distribution port when viewed from vertically above the distribution port; the second drive device moves the second opening-closing portion such that the second opening-closing portion overlaps the distribution port when viewed from vertically above the distribution port, in a same cycle period as that of the first opening-closing portion and at a timing later than that of the first opening-closing portion, and extends from an upstream-side edge of the first opening-closing portion lying on an upstream side of a movement direction of the first opening-closing portion toward the upstream side of the movement direction of the first opening-closing portion, during a time period during which the upstream-side edge of the first opening-closing portion overlaps the distribution port, when viewed from vertically above the distribution port; and the control device is capable of changing a difference between a timing at which the second opening-closing portion overlaps the distribution port when viewed from vertically above the distribution port, and a timing at which the first opening-closing portion overlaps the distribution port when viewed from vertically above the distribution port.

The present invention further provides an apparatus for manufacturing a powder-containing article containing a powder. The apparatus comprises: the above powder supply device; a sheet conveyance device which conveys the sheet along the conveyance path; a second sheet supply section which supplies a second sheet onto a surface of the sheet, at a powder supply position of the conveyance path where the powder is supplied to the sheet or at a position downstream of the powder supply position in a conveyance direction of the sheet; and a bonding device which is provided on the conveyance path, and bonds the sheet and the second sheet together, at a second sheet supply position where the second sheet is supplies from the second sheet supply section onto the surface of the sheet, or at a position downstream of the second sheet supply position in the conveyance direction of the sheet.

The present invention makes it possible to set a holding region holding a powder supplied thereto and a blank region having no powder, in a powder-containing article, respectively, to adequate lengths, easily and separately.

DETAILED DESCRIPTION OF THE INVENTION

With reference to the accompanying drawings, embodiments of the present invention will now be described. It should be understood that the following embodiments are specific examples of the present invention, and are not intended to restrict a technical scope of the present invention.

(1) Powder-Containing Article Manufacturing Apparatus

Figure 1:
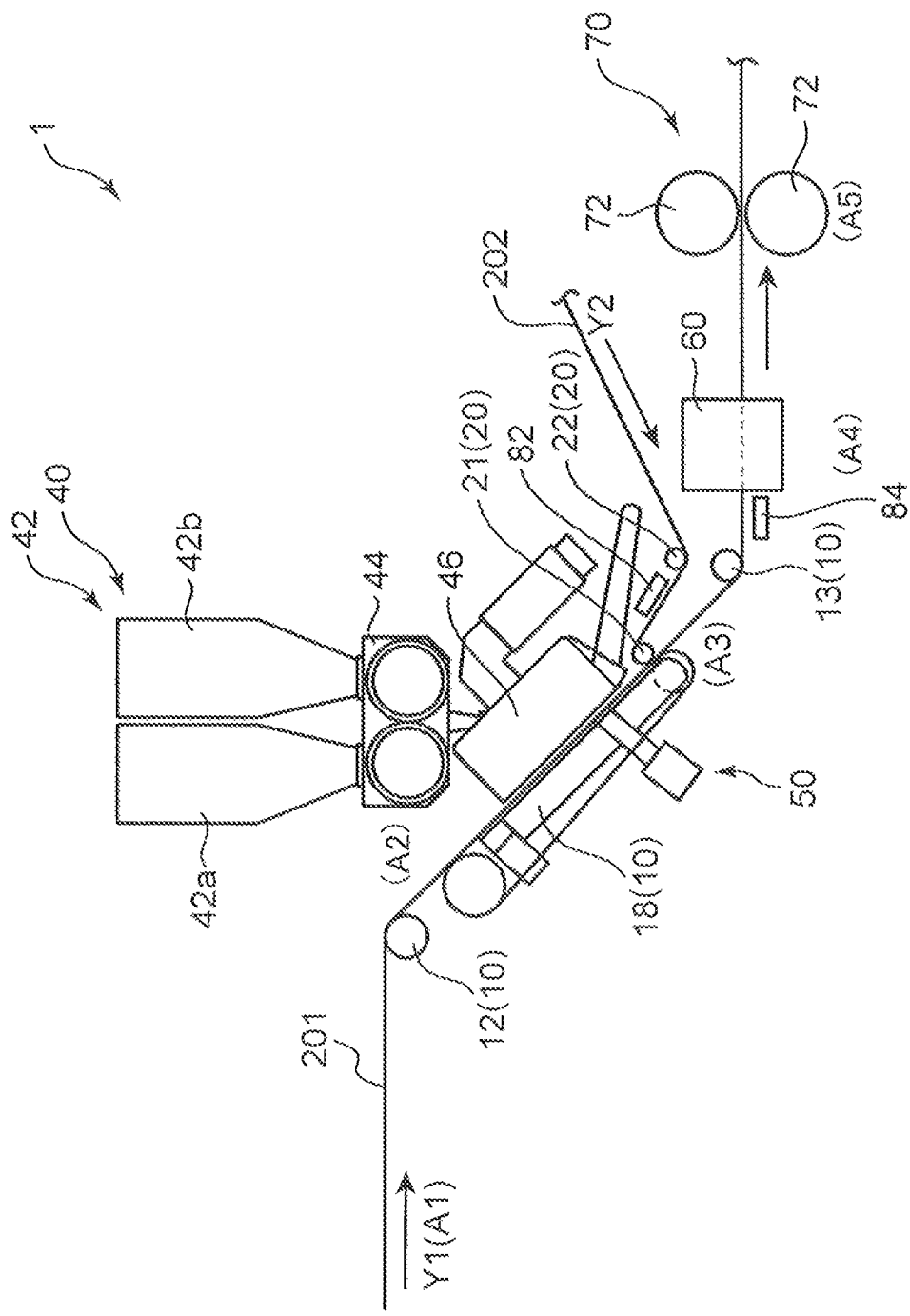
FIG. 1 is a schematic configuration diagram depicting a powder-containing article manufacturing apparatus according to a first embodiment of the present invention.
Figure 2:
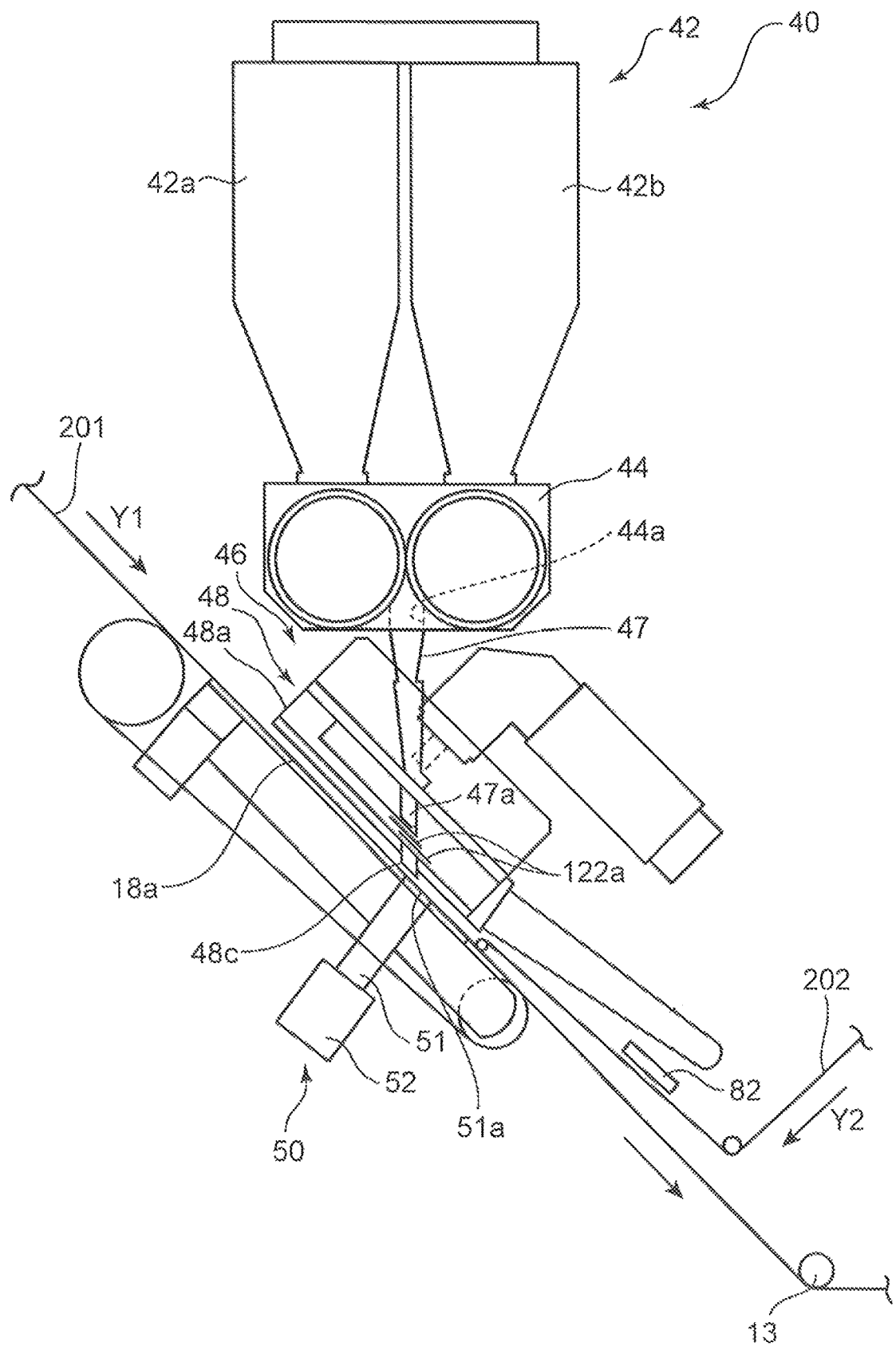
FIG. 2 is a diagram enlargedly depicting a part of FIG. 1.
Figure 3:
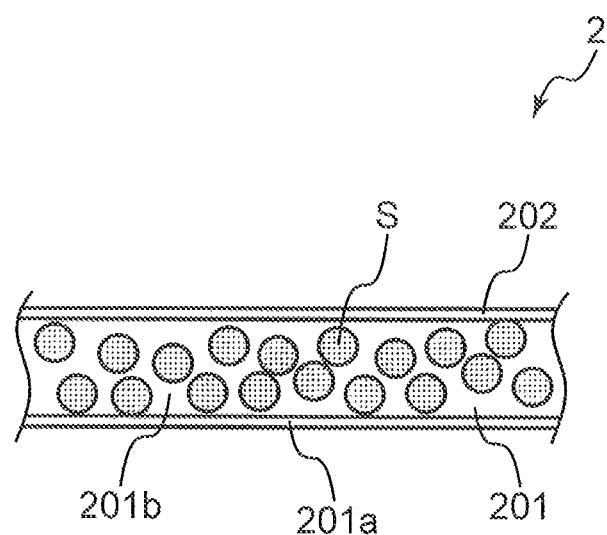
FIG. 3 is a schematic sectional view of a powder-containing article.

FIG. 1 is a schematic diagram depicting a powder-containing article manufacturing apparatus 1 according to a first embodiment of the present invention (hereinafter referred to simply as "manufacturing apparatus 1"). FIG. 2 is a diagram enlargedly depicting a part of FIG. 1, and depicting an internal structure of an aftermentioned powder distribution unit 46.

As depicted in FIG. 1, this manufacturing apparatus 1 comprises a first sheet conveyance device (sheet conveyance device) 10, a second sheet conveyance device 20, a powder supply device 40, a suction device 50, a folding device 60, a pressure-joining device 70, a first adhesive application device 82, and a second adhesive application device 84.

This embodiment will be described based on an example in which a liquid-absorbable powder S is supplied to and held by a first sheet (sheet) 201, and then a second sheet 202 is laminated to and bonded to the first sheet 201 to manufacture a powder-containing article 2, as depicted in FIG. 1. This powder-containing article 2 containing the liquid-absorbable powder S is cut at a plurality of positions and formed into a plurality of discrete articles. Examples of this discrete article include an absorbent body of a disposable diaper.

In this embodiment, a non-woven fabric sheet comprising a bulky layer 201b having a relatively high bulkiness, and a reverse surface layer 201a having a density greater than that of the bulky layer 201b, is used as the first sheet 201, and a tissue paper is used as the second sheet. Further, a powder of SAP (Super Absorbent Polymer) is used as the powder S. The powder S is supplied to the first sheet 201, and introduced and held inside the bulky layer 201b, as described later.

(i) Conveyance Devices

The first sheet conveyance device 10 is a device for conveying the first sheet 201. The first sheet conveyance device 10 comprises a belt conveyer 18, and a plurality of guide rolls 12, 13. In the first sheet conveyance device 10, the belt conveyer 18 is configured to be driven by a motor or the like, so as to convey the first sheet 201 in the direction indicated by the arrowed line Y1 in FIG. 1 along a conveyance path, and sequentially feed the first sheet 201 to the powder supply device 40, the second adhesive application device 84, the folding device 60 and the pressure-joining device 70, in this order.

The second sheet conveyance device 20 is a device for conveying the second sheet 202. The second sheet conveyance device 20 is configured to convey the second sheet 202 toward an obverse surface of the first sheet 201 being conveyed, as indicated by the arrowed line Y2 in FIG. 1. The second sheet conveyance device 20 comprises a motor (not depicted) for feeding out the second sheet 202, and a plurality of guide rolls 21, 22 for guiding the second sheet 202 to the obverse surface of the first sheet 201.

One 21 of the guide rolls functions as a second sheet supply section for supplying the second sheet 202 to the obverse surface of the first sheet 201. Specifically, the guide roll 21 is located adjacent to the obverse surface of the first sheet 201, and the second sheet 202 is guided to the obverse surface of the first sheet 201 by the guide roll 21.

In this embodiment, the guide roll 21 is disposed at a position immediately downstream (in the conveyance direction Y1 of the first sheet 201) of a position opposed to an aftermentioned distribution port 48c of the powder supply device 40, which is a section through which the powder S is supplied to the first sheet S. Thus, the guide roll 21 is operable to supply the second sheet 202 to the obverse surface of the first sheet 201 at a position immediately downstream (in the conveyance direction Y1 of the first sheet 201) of a powder supply position where the powder S is supplied to the first sheet 201, and cover the obverse surface of the first sheet 201 with the second sheet 202.

The first adhesive application device 82 is disposed on a conveyance path of the second sheet 202 at a position upstream of the guide roll 21 in the conveyance direction of the second sheet 202. In this embodiment, the first adhesive application device 82 is disposed at a position immediately upstream of the guide roll 21.

(ii) Powder Supply Device

The powder supply device 40 is a device for intermittently supplying the powder S toward from the obverse surface of the first sheet 201. The powder supply device 40 is operable to drop the powder S onto the obverse surface of the first sheet 201 from thereabove, through the aftermentioned distribution port 48c (see FIG. 4), although details of the powder supply device 40 will be described later.

(iii) Suction Device

The suction device 50 is a device for suctioning a part of the first sheet 201 being conveyed on the belt conveyer 18 from the reverse side of the first sheet 201.

As depicted in FIG. 2, the suction device 50 comprises a suction passage 51 formed with a suction port 51a, and a suction pump 52 connected to the suction passage 51, wherein the suction device 50 is configured to suck in air surrounding the suction port 51a by driving of the suction pump 52. The suction port 51a is disposed around a position opposed to the distribution port 48c. In this embodiment, the suction port 51a extends from a position just below the distribution port 48c to a position downstream of the distribution port 48c in the conveyance direction Y1 of the first sheet 201, so that the suction device 50 can suction the reverse surface of a part of the first sheet 201 passing through the suction port 51a. More specifically, the suction port 51a is disposed on a reverse side of the conveyer belt 18a, and configured to suction the part of the first sheet 201 via a plurality of air holes formed in the conveyer belt 18a.

(iv) Adhesive Application Devices and Folding Device

The first adhesive application device 82 is a device for applying an adhesive to the second sheet 202. For example, the first adhesive application device 82 may be designed to apply a hot-melt adhesive to the second sheet 202. The first adhesive application device 82 is disposed on the conveyance path of the second sheet 202 at a position upstream of the guide roll 21, as mentioned above, and configured to apply an adhesive to a surface of the second sheet 202 at a position before reaching to the obverse surface of the first sheet 201.

Accordingly, the second sheet 202 applied with the adhesive is covered over the first sheet 201 by the guide roll 21, and, during the covering, the first sheet 201 and the second sheet 202 are adhesively bonded together.

As above, in this embodiment, the guide roll 21 functions as a second sheet supply section for supplying the second sheet 202 to the obverse surface of the first sheet 201, and further functions as a bonding device for adhesively bonding the two sheets 201, 202 together.

Further, in this embodiment, the guide roll 21 is configured to pressure-join the two sheets 201, 202 bonded together, in a thickness direction of them. Thus, through the guide roll 21, the first sheet 201 and the second sheet 202 are bonded together while being pressure-joined in the thickness direction of them.

The second adhesive application device 84 is located downstream of the guide roll 21 in the conveyance direction of the first sheet 201. The second adhesive application device 84 is a device for applying an adhesive to part of a region of the second sheet 202 protruding outwardly from the first sheet 201. For example, the second adhesive application device 84 may be designed to apply a hot-melt adhesive to the second sheet 202.

More specifically, in this embodiment, the second sheet 202 is composed of a sheet having a width greater than that of the first sheet 201. Thus, when the second sheet 202 is supplied and bonded to the obverse surface of the first sheet 201 through the guide roll 21, the second sheet 202 on the first sheet 201 will protrude outwardly with respect to the first sheet 201 in the width direction thereof. In this embodiment, width-directional opposite end portions of the second sheet 202 protrude outwardly with respect to the first sheet 201. In this state, the second adhesive application device 84 is operable to apply an adhesive to the width-directional opposite end portions of the second sheet 202.

The folding device 60 is a device for holding the second sheet 202 such that the second sheet 202 enfolds the first sheet 201. More specifically, the folding device 60 is configured to fold the width-directional opposite end portions of the second sheet 202 such that it wraps around the reverse side of the first sheet 201 to extend along the reverse surface of the first sheet 201.

Here, the folding device 60 is located downstream of the second adhesive application device 84 in the conveyance direction of the first sheet 201. In this embodiment, the folding device 60 is located immediately downstream of the second adhesive application device 84.

Thus, when the width-directional opposite end portions of the second sheet 202 applied with the adhesive by the second adhesive application device 84 are folded by the folding device 60, they are bonded to the reverse surface of the first sheet 201.

As above, in this embodiment, the folding device 60 also functions as a bonding device for adhesively bonding the first sheet 201 and the second sheet 202 together.

(v) Pressure-Joining Device

The pressure-joining device 70 is a device for pressure-joining an assembly of the first sheet 201 and the second sheet 202 bonded together. In this embodiment, the pressure-joining device 70 comprises a pair of rollers 72, 72, wherein the pressure joining device 70 is configured to allow the assembly of the first sheet 201 and the second sheet 202 to pass through between the rollers 72, 72 so as to pressure join the assembly in a thickness direction thereof.

(2) Powder Supply Device

A specific structure of the powder supply device 40 will be described.

(i) Overall Configuration

Figure 4:
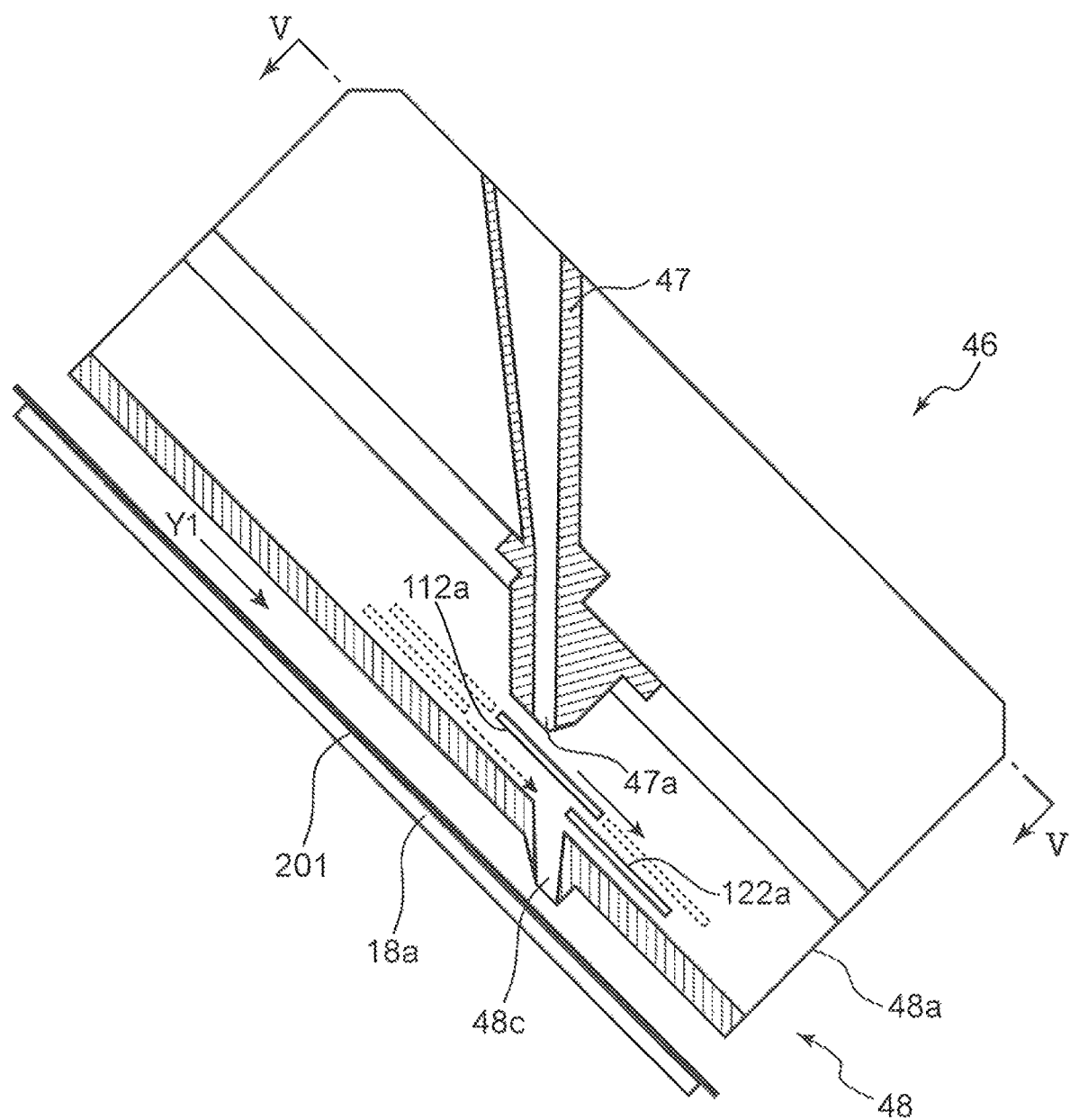
FIG. 4 is a diagram enlargedly depicting an internal structure of a powder supply device.
Figure 5:
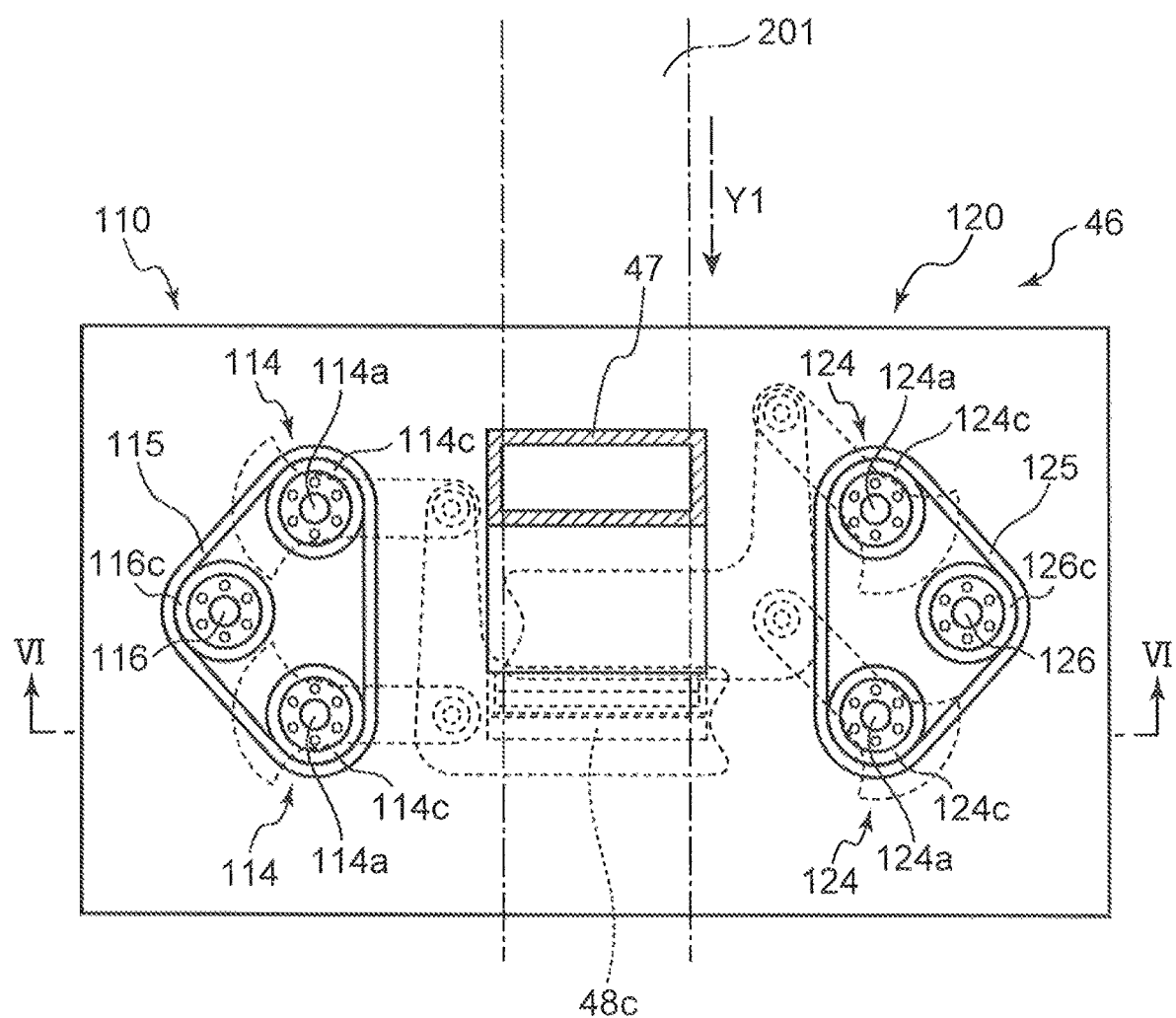
FIG. 5 is a sectional view taken along the line V-V in FIG. 4.
Figure 6:
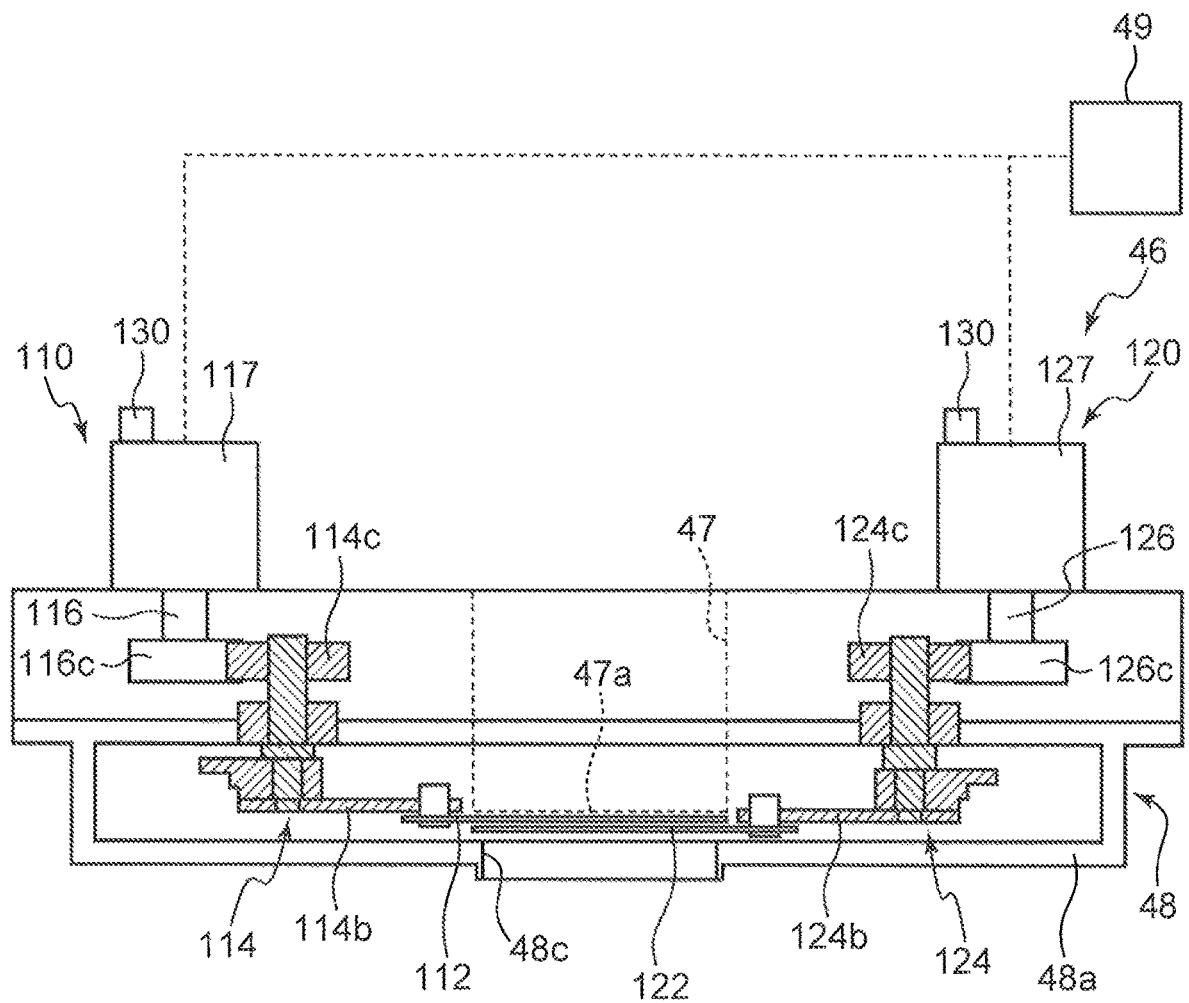
FIG. 6 is a sectional view taken along the line VI-VI in FIG. 5.

The powder supply device 40 comprises a powder storage unit 42, a metering unit 44, a powder distribution unit 46, and a control unit 49 (see FIG. 6). The powder distribution unit 46 comprises a powder guide section 47, and mechanism 48 comprising a housing 48a internally having a relatively wide space. FIG. 4 is a diagram enlargedly depicting a part of FIG. 2. FIG. 5 is a sectional view taken along the line V-V in FIG. 4. FIG. 6 is a sectional view taken along the line VI-VI in FIG. 5.

The powder storage unit 42 is a component storing therein the powder S, as depicted, e.g., in FIGS. 2 and 4. In this embodiment, as depicted, e.g., in FIG. 2, the powder storage unit 42 comprises two tanks 42a, 42b each storing therein the powder S. Each of these two tanks 42a, 42b has a bottom wall formed with an opening for allowing the powder S to drop toward the metering unit 44, so that the powder S is fed to the metering unit 44 via this opening.

The metering unit 44 is a device for metering each of the powders S fed from the tanks 42a, 42b, and feeding the metered powders S to the powder distribution unit 46. The metering unit 44 is configured to continuously convey the powder S fed from each of the tanks 42a, 42b, downwardly at a given flow rate. The powder S to be conveyed falls downwardly from an outlet 44a provided in a bottom wall of the metering unit 44.

The powder guide section 47 is a component for guiding the powder S falling from the outlet 44a of the metering unit 44, downwardly. The powder guide section 47 is composed of a vertically-extending tubular member which is internally formed with a space communicating with the outlet 44a. The powder S falling from the outlet 44a of the metering unit 44 flow through the powder guide section 47, and then fall downwardly from a powder supply port 47a formed at a lower end of the powder guide section 47.

As above, in this embodiment, the powder storage unit 42 and the metering unit 44 function as a storage section storing therein the powder S, and the powder S falls through the powder guide section 47 and the powder supply port 47a.

As depicted in FIG. 4, the lower end of the powder guide section 47 formed with the powder supply port 47a is inserted into the housing 48a through a top wall of the housing 48a, so that the powder S falling from the powder supply port 47a flows into the housing 48a.

A bottom wall of the housing 48a has a distribution port 48c which is formed at a position opposed to the powder supply port 47a to penetrate the bottom wall in an upward-rearward direction. More specifically, the distribution port 48c is disposed at a position spaced apart vertically downwardly from the powder supply port 47a, and overlapping the powder supply port 47a when as viewed along the vertical direction. Accordingly, the powder S discharged from the powder supply port 47a falls toward the distribution port 48c.

The belt conveyer 18 is disposed beneath the distribution port 48c, so that the powder S falling toward the distribution port 48c is supplied onto the obverse surface of the first sheet 201 at a position on the belt conveyer 18 through the distribution port 48c.

Figure 7A:
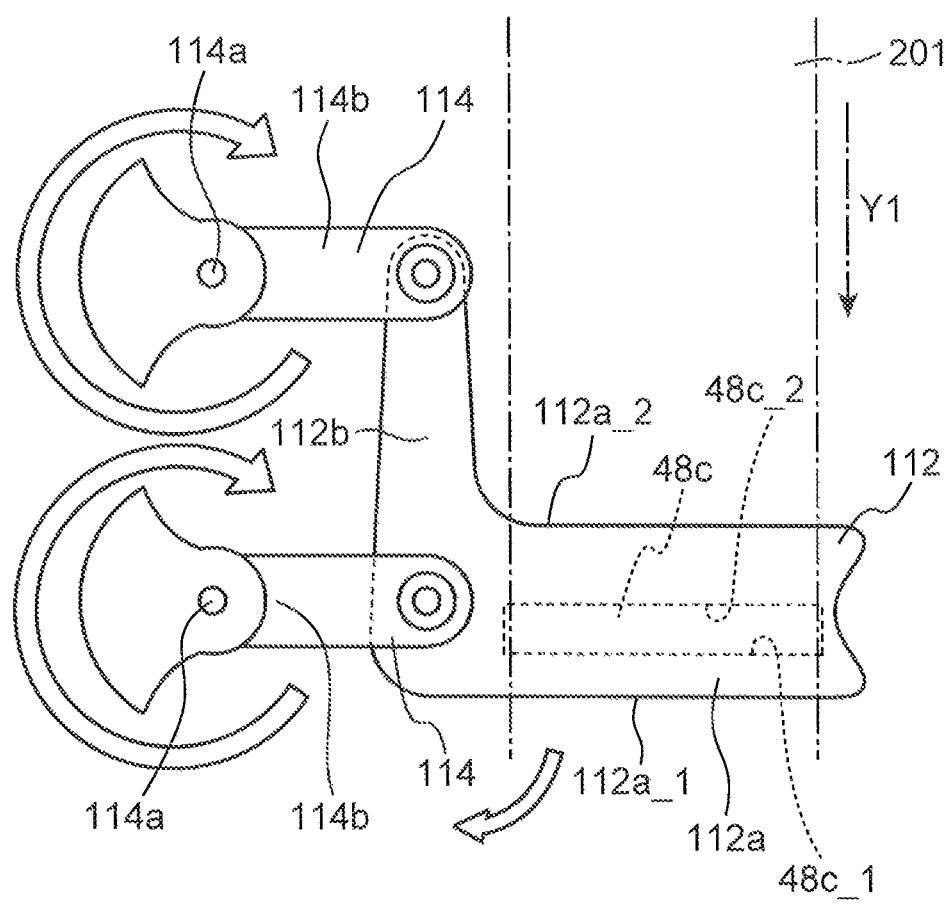
FIG. 7A is a diagram depicting a state in which a first opening-closing portion closes a distribution port.

As depicted in FIG. 7A which depicts an internal structure of the housing 48a, in this embodiment, the distribution port 48c is formed in a rectangular shape which extends in a width direction of the first sheet 201, i.e., a direction orthogonal to the conveyance direction Y1 of the first sheet 201 and parallel to the obverse surface of the first sheet 201, and has a first opening edge 48c_1 located on a downstream side of the conveyance direction Y1 of the first sheet 201 and extending parallel to the width direction of the first sheet 201 and a second opening edge 48c_2 located on an upstream side of the conveyance direction Y1 of the first sheet 201 and extending parallel to the width direction of the first sheet 201.

As depicted in FIG. 4, the belt conveyer 18 is disposed such that a downstream end region, in the conveyance direction Y1 of the first sheet 201, of a conveyer belt 18a thereof on which the first sheet 201 is placed is located downward of an upstream end region of the conveyer belt 18a in the conveyance direction Y1 of the first sheet 201. Thus, at a position opposed to the distribution port 48c, the first sheet 201 receives supply of the powder S from above while being conveyed obliquely downwardly with respect to the vertical direction. As above, in this embodiment, the first sheet 201 and the powder S are moved obliquely downwardly with respect to the vertical direction. Thus, a situation is suppressed in which particles of the powder S dropped from the distribution port 48c onto the first sheet 201 bounce from and partly drop out of the first sheet 201, so that the powder S efficiently stays on the first sheet.

Further, the bottom wall of the housing 48a extends parallel to the obverse surface of a part of the first sheet 201 on the belt conveyer 18. The bottom wall of the housing 48a is disposed at a position adjacent to the obverse surface of a part of the first sheet 201 on the belt conveyor 18, so that the distribution port 48c is located adjacent to the obverse surface of the part of the first sheet 201. Thus, the powder S dropped from the distribution port 48c is efficiently supplied to the first sheet 201.

Here, the metering unit 44 continuously conveys the powder S downwardly, as mentioned above, so that the powder S continuously falls from the powder supply port 47a toward the distribution port 48c. However, in this embodiment, two shutter units 110, 120 (first shutter unit 110, and second shutter unit) provided in the mechanism 48 are operable to intermittently restrict the powder S from reaching the first sheet 201. This allows the powder S to be intermittently supplied to the first sheet 201.

(ii) Shutter Units

Next, the shutter units 110, 120 will be described.

As depicted, e.g., in FIGS. 5 and 6, the first shutter unit 110 and the second shutter unit 120 are provided, respectively, on both sides of the distribution port 48c along a longitudinal direction of the distribution port 48c.

In the following description about the shutter units 110, 120, the longitudinal direction of the distribution port 48c which is the width direction of a part of the first sheet 210 passing through below the distribution port 48c, i.e., a rightward-leftward direction in FIGS. 5 and 6, will be referred to simply as "the rightward-leftward direction", and one side on which the first shutter unit 110 is disposed and the other side on which the second shutter unit 120 is disposed will be referred to respectively as "the left side" and "the right side".

Figure 7B:
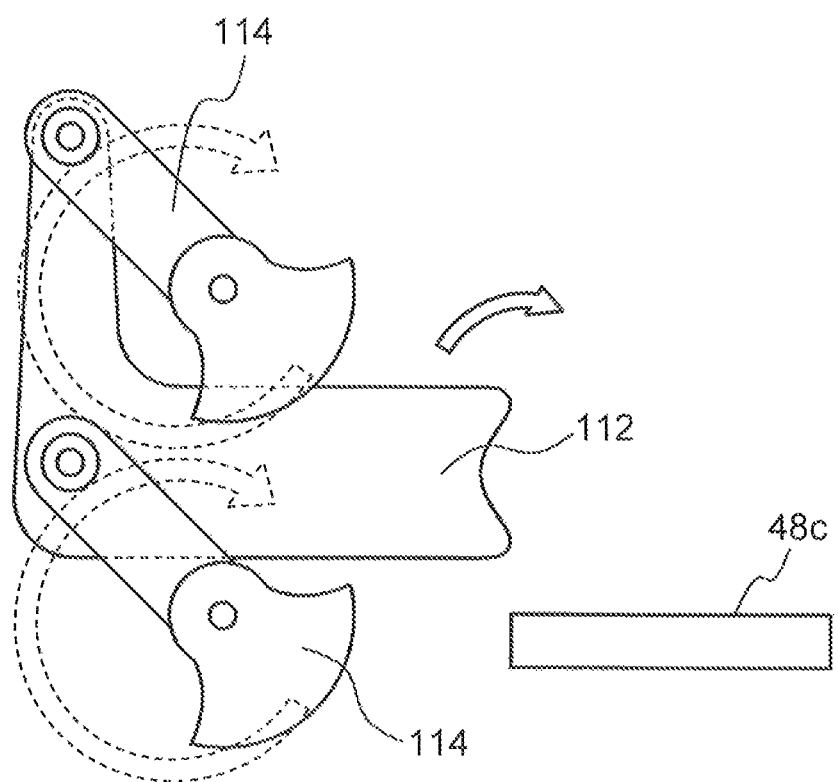
FIG. 7B is an explanatory diagram of the movement of the first opening-closing portion.

FIGS. 7A and 7B are explanatory diagrams of a detailed structure of an aftermentioned shutter plate 112, wherein the inside of the housing 48a is depicted in a state in which the second shutter unit 120 and others are omitted. FIGS. 7A and 7B are diagrams when viewed from a direction orthogonal to the bottom wall of the housing 48a.

The first shutter unit 110 comprises a shutter plate 112, a pair of link members 114, 114 coupled to the shutter plate 112, an output shaft 116 coupled to the link members 114, 114 via a belt 115, and a motor (first drive device) 117 for rotationally driving the output shaft 116.

The shutter plate 112 is a plate-shaped member. The shutter plate 112 has a first opening-closing portion 112a extending in the rightward-leftward direction, and a coupling portion 112b extending from a left end of the first opening-closing portion 112a in a direction orthogonal to the rightward-leftward direction (a width direction of the first opening-closing portion 112a). The shutter plate 112 extends parallel to the bottom wall of the housing 48a.

As depicted, e.g., in FIGS. 4 and 7A, the first opening-closing portion 112a has a shape capable of, in a state in which it is located just above the distribution port 48c, overlapping the entire distribution port 48c and closing the entire distribution port 48c from thereabove, when viewed from vertically above the distribution port 48c.

Each of width-directional opposite edges, i.e., one edge 112a_1 and the other edge 112a_2, of the first opening-closing portion 112a extends straight in the rightward-leftward direction.

The link members 114, 114 are arranged side-by-side on the left side of the distribution port 48c along a direction parallel to a width direction of the distribution port 48c.

Each of the link members 114, 114 comprises a column-shaped shaft 114a extending in an upward-downward direction, and a link plate 114b extending from an outer peripheral surface of the shaft 114a outwardly in a radial direction of the shaft 114a.

Specifically, each of the shafts 114a, 114a extends in a direction orthogonal to the bottom wall of the housing 48a, and each of the link plates 114b, 114b extends in a direction parallel to the bottom wall of the housing 48a.

Each of the shafts 114a, 114a is fixed to the housing 48a rotatably about its center line, and each of the link plates 114b, 114b is configured such that one of opposite ends, i.e., a base end, thereof is fixed to a corresponding one of the shafts 114a, 114a rotatably together with the shaft 114a.

The shutter plate 112 is rotatably coupled to each of the other ends, i.e., distal ends, of the link plates 114b, 114b. Longitudinal opposite ends of the coupling portion 112b of the shutter plate 112 are coupled, respectively, to the distal ends of the link plates 114b, 114b.

The output shaft 116 is a column-shaped member extending parallel to the shafts 114a, 114a of the link members 114, 114, and is configured to be driven by the motor 117 so as to be rotated about its center line, as mentioned above.

The output shaft 116 is coupled to the shafts 114a, 114a of the link member 114, 114 via the belt 115. Thus, when the output shaft 116 is rotationally driven by the motor 117, the shafts 114a, 114a of the link member 114, 114 are also synchronously rotated about their center lines.

Upon rotation of the shafts 114a, 114a of the link member 114, 114, along with rotation of the link plates 114b, 114b, the shutter plate 112 is rotated from a state depicted in FIG. 7A to a state depicted in FIG. 7B, while maintaining a posture where the first opening-closing portion 112a extends in the rightward-leftward direction. As above, in this embodiment, the two link members 114, 114 and the shutter plate 112 forms a four-bar link mechanism. Further, the shutter plate 112 is configured to be rotated in a plane parallel to the bottom wall of the housing 48a along a trajectory passing just above the distribution port 48c, while maintaining the posture where the first opening-closing portion 112a extends in the rightward-leftward direction.

As depicted, e.g., in FIGS. 4 and 7A, the shutter plate 112 is disposed at a position where the first opening-closing portion 112a thereof can periodically overlap the distribution port 48c, when viewed from vertically above the distribution port 48c, to close the entire distribution port 48c, so that the first opening-closing portion 112a can periodically close the distribution port 48c along with rotation of the shutter plate 112.

When the distribution port 48c is closed by the first opening-closing portion 112a, the powder S falling from the powder supply port 47a toward the distribution port 48c bounces from the first opening-closing portion 112a and is then received by the bottom wall of the housing without reaching the distribution port 48c, so that supply of the powder S is stopped.

As depicted, e.g., in FIG. 7A, a direction along which the shutter plate 112 is moved just above the distribution port 48c is set to the same direction as the conveyance direction Y1 of the first sheet 201 indicated by the arrowed line Y1, so that the first opening-closing portion 112a is moved to close the distribution port 48c from the upstream side toward the downstream side of the conveyance direction Y1 of the first sheet 201. Further, the first opening-closing portion 112*a* is moved just above the distribution port 48*c* obliquely downwardly with respect to the vertical direction. In the present invention, a movement direction of of the shutter plate 112 is not particularly limited. However, moving the first opening-closing portion 112*a* obliquely downwardly in the above manner is preferable because it makes it possible to reduce resistance against dropping of particles of the powder S and suppress scattering of the particles of the powder S in the housing 48*a*.

Figure 8:
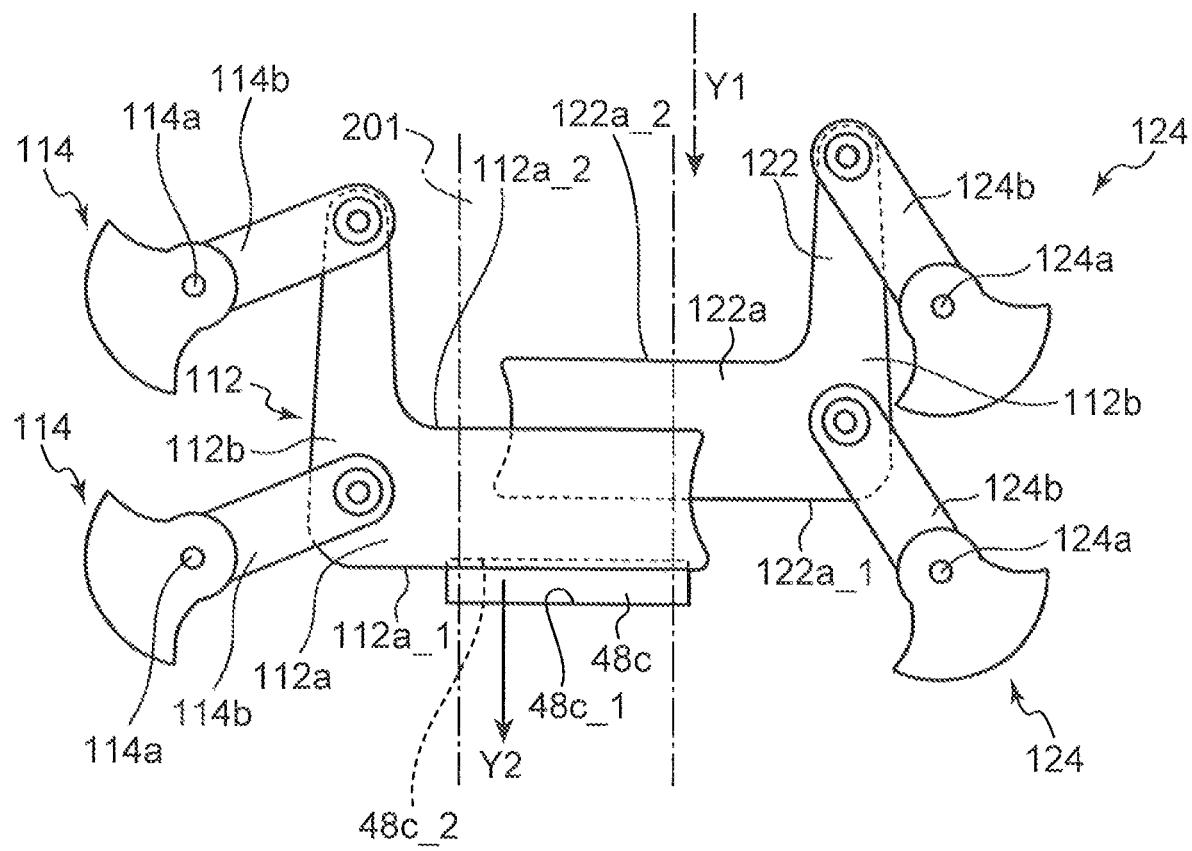
FIG. 8 is a diagram depicting a state at a time when the first opening-closing portion starts to pass through above the distribution port.

FIG. 8 is a diagram depicting the inside of the housing 48*a*. As depicted, e.g., in FIGS. 8, 5 and 6, the second shutter 120 has approximately the same structure as that of the first shutter unit 110. It should be noted that FIG. 8 and aftermentioned FIGS. 9 and 10 corresponding to FIG. 8 also depict states when viewed from the direction orthogonal to the bottom wall of the housing 48*a*, as with, e.g., FIGS. 7A and 7B.

Specifically, as with the first shutter unit 110, the second shutter unit 120 comprises: a shutter plate 122 having a second opening-closing portion 122*a* and a coupling portion 122*b*; a pair of link members 124, 124 each comprising a shaft 124*a* and a link plate 124*b* and coupled to the shutter plate 122; an output shaft 126 coupled to the link members 124, 124 via a belt 125; and a motor (second drive device) 127 for rotationally driving the output shaft 126.

The second shutter unit 120 is also configured such that the second opening-closing portion 122*a* is rotationally moved in a plane parallel to the bottom wall of the housing 48*a*, while maintaining a posture where it extends in the rightward-leftward direction, and periodically overlaps the distribution port 48*c*, when viewed from vertically above the distribution port 48*c*, to close the entire distribution port 48*c*. Further, in the second shutter unit 120, each of widthdirectional opposite edges, i.e., one edge 122*a*_1 and the other edge 122*a*_2, of the second opening-closing portion 122*a* also extends straight in the rightward-leftward direction.

On the other hand, the second shutter unit 120 is formed in a configuration having a bilaterally symmetric relationship with that of the first shutter unit 110. Further, the shutter plate 122 of the second shutter unit 120 is configured to be rotated in a direction opposite to that in the first shutter unit 110. Accordingly, as with the first shutter unit 110, in the second shutter unit 120, the second opening-closing portion 122*a* of the shutter plate 122 can close the distribution port 48*c* from the upstream side toward the downstream side of the conveyance direction Y1 of the first sheet 201.

(iii) Control Unit

The control unit 49 is designed to control the motor 117 of the first shutter unit 110 and the motor 127 of the second shutter unit 120.

In this embodiment, by the control unit 49, the motor 117 of the first shutter unit 110 and the motor 127 of the second shutter unit 120 are set to be constant in terms of rotational speed during one cycle period, and identical in terms of rotation cycle period. Therefore, the opening-closing portion 112*a*, 122*a* of the shutter units 110, 120 have the same rotational speed, and can overlap and close the distribution port 48*c* in the same cycle period.

However, as depicted, e.g., in FIG. 4, the shutter plate 122 of the second shutter unit 120 is disposed such that it passes through above the distribution port 48*c* at a position below the shutter plate 112 of the first shutter unit 110.

Further, the control unit 49 is operable to set and change respective rotational phases of the motor 117 of the first shutter unit 110 and the motor 127 of the second shutter unit 120. In this embodiment, the control unit 49 is electrically connected to these motors 117, 127, and comprises an input section, wherein it is operable, based on a value input into the input section, to set and change respective rotation start timings of the motors 117, 127. By changing the rotation start timings of the motors 117, 127, an amount of a difference between a timing at which the first openingclosing portion 112*a* overlaps the distribution port 48*c* and a timing at which the second opening-closing portion 122*a* overlaps the distribution port 48*c* is changed. Two sensors 130, 130 are installed, respectively, to the motors 117, 127 to detect respective rotational positions, i.e., rotational phases, thereof, and, based on a result of detections of the sensors 130, 130, the difference amount is adjusted to a given value.

Here, the timing at which the opening-closing portion 112*a* (122*a*) overlaps the distribution port means a beginning or an end of a time period during which each of the opening-closing portions 112*a*, 122*a* overlaps the distribution port 48*c*. More specifically, the beginning is a timing at which the downstream-side edge 112*a*_1 (122*a*_1) of the opening-closing portion 112*a* (122*a*) lying on an downstream side of a movement direction of the opening-closing portion 112*a* (122*a*) overlaps the upstream-side (second) opening edge 48*c*_2 of the distribution port 48*c* lying on an upstream side of the movement direction of the opening-closing portion 112*a* (122*a*), and the end is a timing at which the upstream-side edge 112*a*_2 (122*a*_2) of the opening-closing portion 112*a* (122*a*) lying on the upstream side of the movement direction of the opening-closing portion 112*a* (122*a*) overlaps the downstream-side (first) opening edge 48*c*_1 of the distribution port 48*c* lying on the downstream side of the movement direction of the opening-closing portion 112*a* (122*a*). The timing at which the openingclosing portion 112*a* (122*a*) overlaps the distribution port (overlapping timing of the opening-closing portion 112*a* (122*a*) with the distribution port) is one of them. Further, the "difference" in the overlapping timing means a temporal difference (time lag) between respective overlapping timings of the downstream-side edges 112*a*_1, 122*a*_1 of the opening-closing portions 112*a*, 122*a* with the upstream-side opening edge 48*c*_2 of the distribution port 48*c*, or between respective overlapping timings of the upstream-side edges 112*a*_2, 122*a*_2 of the opening-closing portions 112*a*, 122*a* with the downstream-side opening edge 48*c*_1 of the distribution port 48*c*, on the basis of the movement direction of each of the opening-closing portions 112*a*, 122*a*.

In this embodiment, respective overlapping timings of the opening-closing portions 112*a*, 122*a* with the distribution port 48*c* are set by the control unit 49 in the following manner.

Figure 9:
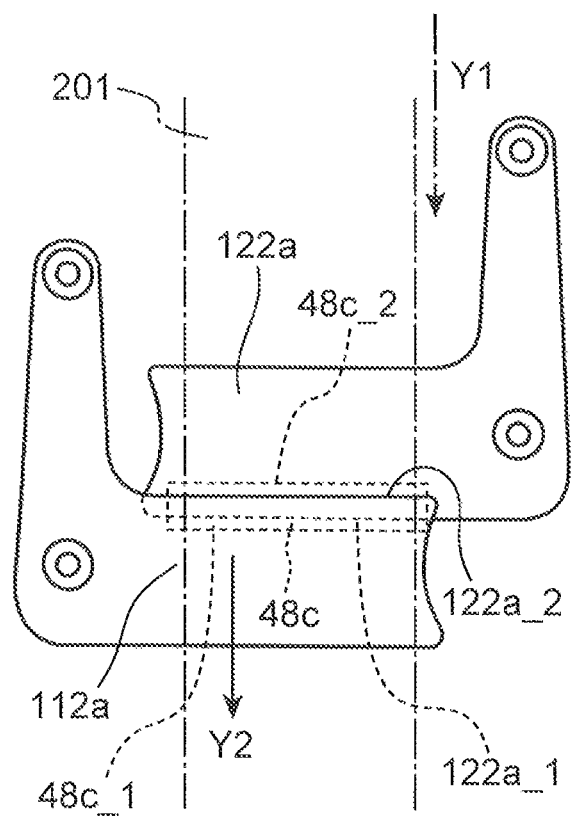
FIG. 9 is a diagram depicting a state at a time when the first opening-closing portion and a second opening-closing portion are passing through above the distribution port.
Figure 10:
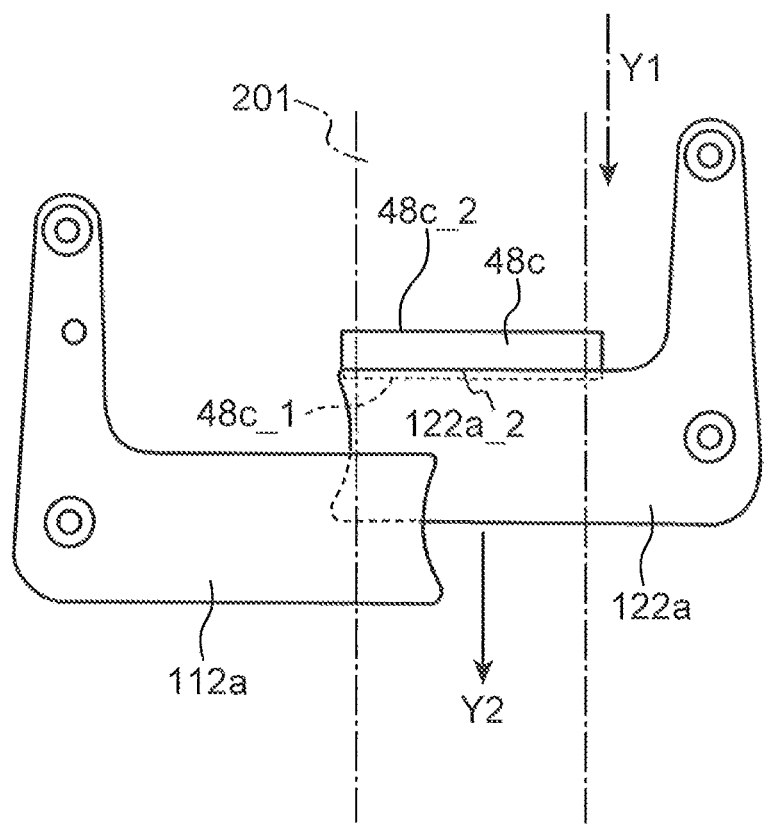
FIG. 10 is a diagram depicting a state at a time just before the second opening-closing portion completes the passing through above the distribution port.

FIGS. 9 and 10 are diagrams corresponding to FIG. 2, and depicting states during a time period during which the first opening-closing portion 112*a* and a second opening-closing portion 122*a* overlap the distribution port 48*c*, wherein time progresses in the following order: FIG. 8, FIG. 9 and FIG. 10.

The above overlapping timings are set such that, after the first opening-closing portion 112*a* starts to pass through above the distribution port 48*c* and overlaps the distribution port 48*c*, the second opening-closing portion 122*a* starts to pass through above the distribution port 48*c* and overlaps the distribution port 48*c*, at a position below the first openingclosing portion 112*a*.

Further, as depicted in FIGS. 8 to 10, the motors 117, 127 and the opening-closing portions 112*a*, 122*a* are controlled such that, during a time period during which at least the upstream-side edge 112*a*_2 of the first opening-closing portion 112a lying on the upstream side of the rotation (movement) direction of the first opening-closing portion 112a overlaps the distribution port 48c, when viewed from vertically above the distribution port 48c, the second opening-closing portion 122a extends from the rotation directional upstream-side edge 112a_2 toward the upstream side of the rotational direction of the first opening-closing portion 112a. That is, just when or before the upstream-side edge 112a_2 of the first opening-closing portion 112a passes through above the second opening edge 48c_2 of the distribution port 48c, the downstream-side edge 122a_1 of the second opening-closing portion 122a lying on the downstream side of the rotation (movement) direction of the second opening-closing portion 122a passes through above the second opening edge 48c_2 of the distribution port 48c, and, during the time period during which the rotation directional upstream-side edge 112a_2 of the first opening-closing portion 112a overlaps the distribution port 48c, both of the first opening-closing portion 112a and the second opening-closing portion 122a overlap the distribution port 48c.

Based on this configuration, during a time period after the rotation directional downstream-side edge 112a_1 of the first opening-closing portion 112a passes through above the first opening edge 48c_1 of the distribution port 48c through until the rotation directional upstream-side edge 122a_2 of the second opening-closing portion 122a passes through above the second opening edge 48c_2 of the distribution port 48c, the distribution port 48c is continuously closed by the opening-closing portions 112a, 122a, so that supply of the powder S to the first sheet 201 is stopped over a longer time period as compared to the case where each of the opening-closing portions 112a, 122a closes the distribution port 48c, separately.

FIGS. 8, 9 and 10 are diagrams when viewed from the direction orthogonal to the bottom wall of the housing 48a inclined with respect to the vertical direction, as mentioned above. However, even when viewed from vertically above the distribution port 48c, the first opening-closing portion 112a and the second opening-closing portion 122a partly overlap each other and cooperatively close the distribution port 48c in the same manner as that depicted in these figures.

Figure 11:
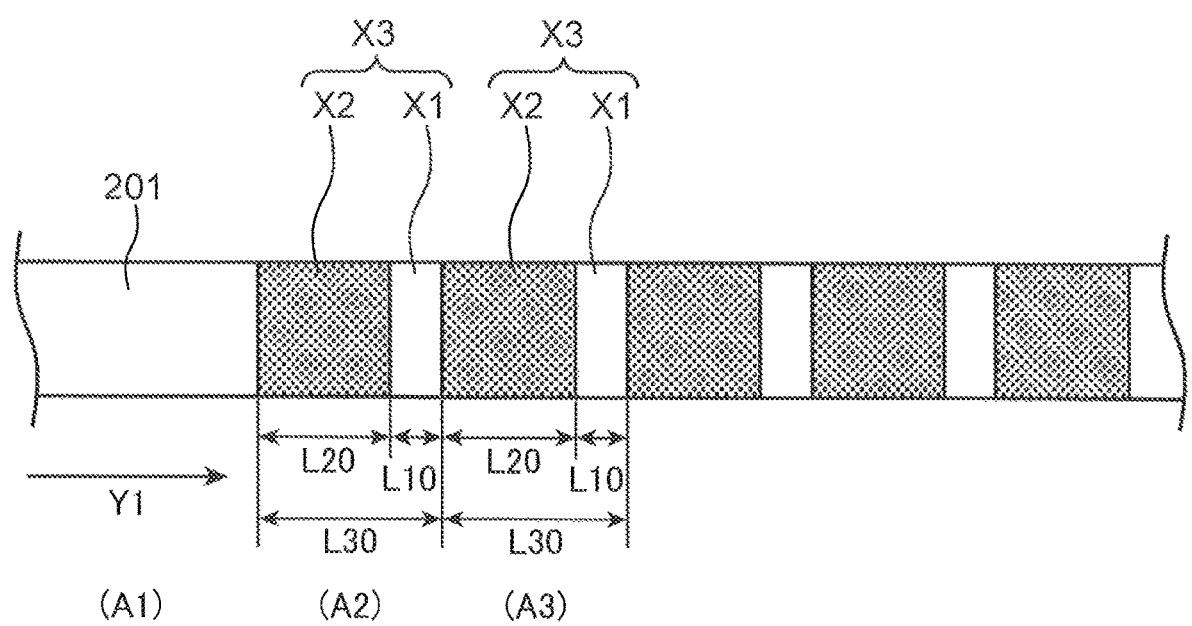
FIG. 11 is a chart presenting the distribution of a powder S on a first sheet.

In this way, in this embodiment, supply of the powder S to the first sheet 201 is stopped by the partly-overlapping first and second opening-closing portions 112a, 122a, so that a blank region X1 devoid of the powder S due to no supply of the powder S, and a holding region X2 holding the powder S supplied thereto, are alternately formed in the first sheet, as depicted in FIG. 11.

Here, each of the first opening-closing portion 112a and the second opening-closing portion 122a is rotated while maintaining a posture where it extends in the rightward-leftward direction, and each of the rotation directional downstream-side edge 112a_1 of the first opening-closing portion 112a and the rotation directional upstream-side edge 112a_2 of the second opening-closing portion 122a is moved just above the distribution port 48c, in a posture where it extends in the rightward-leftward direction, as mentioned above. Thus, as depicted in FIG. 11, a border line between the blank region X1 and the holding region X2 is formed as a line extending in a direction orthogonal to the conveyance direction of the first sheet 201.

Further, in this embodiment, each of the first opening edge 48c_1 and the second opening edge 48c_2 of the distribution port 48c extends parallel to the width direction of the first sheet 201, as mentioned above. Thus, during passing of the first opening-closing portion 112a, the distribution port 48c will be gradually closed in a uniform manner in the width direction of the first sheet 201, and then, during passing of the second opening-closing portion 122a, the distribution port 48c will be gradually opened in a uniform manner in the width direction of the first sheet 201. Therefore, for example, in the case where the powder S is supplied from the distribution port 48c to the first sheet 201 uniformly in the width direction of the first sheet 201, the powder S is supplied to the first sheet 201 uniformly in its width direction, even during a time period from a time when the first opening-closing portion 112a starts to close the distribution port 48c through until the distribution port 48c is fully closed and during a time period from a time when the second opening-closing portion 122a starts to open the distribution port 48c through until the distribution port 48c is fully opened.

Then, when the overlapping timings of the opening-closing portions 112a with the distribution port 48c or the overlapping timings of the opening-closing portions 122a is changed by the control unit 49, an amount by which the opening-closing portions 112a, 122a overlap the distribution port 48c at a position just above the distribution port 48c is changed. Accordingly, a time period during which the distribution port 48c is continuously closed by the opening-closing portions 112a, 122a is changed, so that the length L10 (in the conveyance direction Y1 the first sheet 201) of the blank region X1 is changed.

For example, when the timing at which the second opening-closing portion 122a starts to overlap the distribution port 48c is advanced, the amount of overlapping between the first opening-closing portion 112a and the second opening-closing portion 122a in their movement direction is increased, so that a time period during which the distribution port 48c is continuously closed by the opening-closing portions 112a, 122a is shortened. Therefore, in this case, in the first sheet 201, the length L10 of the region X1 receiving no supply of the powder S is reduced.

Here, the length L30 of a region X3 as a sum of the blank region X1 and the holding region X2 is determined by the cycle period of each of the opening-closing portions 112a, 122a. Thus, by changing the above overlapping timing in a state in which this cycle period is set to a given value, the length L10 of the blank region X1 can be set and changed, independently of the length L30 of the region X3. Therefore, the length X2 of the holding region X2 obtained by subtracting the length L10 of the blank region X1 from the length L30 of the region X3, and the length L10 of the blank region X1, can be set and changed separately.

More specifically, by setting, to a given value, the rotation period, i.e., a movement time period per 360-degree rotation, of each of the opening-closing portions 112a, 122a, the length L30 of the region X3 as the sum of the blank region X1 and the holding region X2 is set to a given value. Thus, to change the length L30, i.e., the length L30 of the discrete article formed by cutting an obtained powder-containing article 2 in the blank region X1 (this length will hereinafter be referred to occasionally as "discrete article length"), the rotation period of each of the opening-closing portions 112a, 122a may be changed.

Here, if the overlapping timings of the opening-closing portions 112a, 122a with the distribution port 48c cannot be changed, a ratio of the length L10 of the blank region X1 to the discrete article length L30 is fixedly set to a given value. Therefore, in this case, for example, the length L10 of the blank region X1 is undesirably increased along with an increase in the discrete article length L30.

Compared to this, in this embodiment, the rotation period of each of the opening-closing portions 112a, 122a can be set to a given value to set the discrete article length L30 to a given value, and then at least one of the above overlapping timings can be changed to change the length L10 of the blank region X1 while maintaining the discrete article length L30 at the given value. Accordingly, the length L20 of the holding region X2 can be set and changed, independently from the discrete article length L30

For example, in the case where the blank region X1 requires only a function of being cut, the blank region X1 needs not be excessively increased in length, because it is only necessary for the blank region X1 to have a length enough to simply enable cutting in this region X1. Further, there is a situation where, with a view to enabling each discrete article to contain a large amount of powder, it is desired to increase a ratio of the length L20 of the holding region X2 to the discrete article length L30 is increased, i.e., reduce the length L10 of the blank region X1. In this situation, by setting the rotation period of each of the opening-closing portions 112a, 122a to a given value, and then setting the temporal difference between the overlapping timings of the opening-closing portions 112a, 122a with the distribution port 48c, to a relatively small value, the length L10 of the blank region X1 can be reduced while setting the discrete article length L30 to a desired value.

(3) Powder Supply Method

A method for supplying the powder S to the first sheet 201 being conveyed along the conveyance path, by using the above powder supply device 40 will be described below.

This method implements a distribution step of dropping a given amount of powder S from the metering unit 44 to distribute the powder S onto the obverse surface of the first sheet 201 through the distribution port 48c, according to a conveyance speed of the first sheet 201.

During implementation of the distribution step, the method implements a first closing step of rotating the first opening-closing portion 112a such that it periodically overlaps the distribution port 48c when viewed from vertically above the distribution port 48c, to periodically close the distribution port 48c by the first opening-closing portion 112a, and a second closing step of rotating the second opening-closing portion 122a such that it overlaps the distribution port 48c when viewed from vertically above the distribution port 48c, in the same cycle period as that of the first opening-closing portion 112a and at a timing later than that of the first opening-closing portion 112a, to periodically close the distribution port 48c by the second opening-closing portion 122a.

In the second closing step, the second opening-closing portion 122a is rotated such that it extends from the rotation directional upstream-side edge 112a_2 of the first opening-closing portion 112a, during a time period during which the rotation directional upstream-side edge of the first opening-closing portion 112a overlaps the distribution port 48c, when viewed from vertically above the distribution port 48c. In this embodiment, during this step, the second opening-closing portion 122a is rotated to pass through the distribution port 48c at a position below the first opening-closing portion 112a. In this method, the cycle period of each of the first opening-closing portion 112a and the second opening-closing portion 122a is preliminarily set to an adequate value, according to the conveyance speed of the first sheet 201 and the discrete article length L30.

The method further implements a timing setting step of setting a difference between a timing at which the second opening-closing portion 122a overlaps the distribution port 48c when viewed from vertically above the distribution port 48c, and a timing at which the first opening-closing portion 112a overlaps the distribution port 48c when viewed from vertically above the distribution port 48c, such that the length L10 of the blank region X1 becomes a given value.

This method makes it possible to intermittently supply the powder S to the first sheet 201 at given intervals so as to form the blank region X1 and the holding region X2 each having a given length.

(4) Powder-Containing Particle Manufacturing Method

Next, the procedure of a method for manufacturing a powder-containing article 2 by the manufacturing apparatus comprising the powder supply device 40 will be described with reference to FIG. 1.

First of all, a difference between a timing at which the second opening-closing portion 122a overlaps the distribution port 48c when viewed from vertically above the distribution port 48c, and a timing at which the first opening-closing portion 112a overlaps the distribution port 48c when viewed from vertically above the distribution port 48c is set as mentioned above (timing setting step).

Subsequently, the first sheet 201 is conveyed along the conveyance path at a given conveyance speed (conveyance step A1). In this embodiment, the first sheet 201 is conveyed by the first sheet conveyance device 10.

Subsequently, a given amount of powder S is supplied onto the obverse surface of the first sheet 101. Specifically, the distribution step, the first closing step and the second closing step are implemented to intermittently supply the powder S to the first sheet 201 (powder supply step A2).

In this embodiment, during this step, the first sheet 201 is suctioned from the reverse side thereof by the suction device 50.

Subsequently, through the guide roll 21, a second sheet 202 is supplied to the obverse surface of the first sheet 201 after being supplied with the powder S (second sheet supplying step A3). In this embodiment, the guide roll 21 of the second sheet conveyance device 20 is located downstream of a position opposed to the distribution port 48c, so that the second sheet 202 is supplied to the obverse surface of the first sheet 201 at a position just after the powder S is supplied to the first sheet 201, as mentioned above. During the second sheet supplying step, after an adhesive is applied onto the second sheet 202 by the first adhesive application device 82, the second sheet 202 is supplied to the obverse surface of the first sheet 201. Further, through the guide roll 21, the first sheet 201 and the second sheet 202 are bonded together while pressure joining them in their thickness direction (first bonding step A3, bonding step).

Subsequently, after an adhesive is applied onto the supplied second sheet 202 by the second adhesive application device 84, the second sheet 202 is folded to bond the two sheets 201, 202 together, by the folding device 60 (second bonding step A4, bonding step).

Last of all, the assembly of the first sheet 201 and the second sheet 202 bonded together is pressure-joined in a thickness direction thereof by the pressure-joining device 70, to manufacture a powder-containing article 2 containing the liquid-absorbable powder S. After passing through the pressure-joining device 70, the particle-containing article is appropriately cut in the blank region X1 thereof in which the powder S is not placed, and used as an absorbent body of a diaper or the like. The particle-containing article is cut in the region in which the powder S is not placed, so that it is possible to suppress leakage of the powder S through the resulting cut surface. In addition, it is possible to suppress damage to a cutter blade for use in the cutting, due to interference with particles of the powder S.

Through this method, a powder-containing article 2 is manufactured in which the powder S is intermittently disposed between the first sheet 201 and the second sheet 202. Further, a difference between a timing at which the second opening-closing portion 122a overlaps the distribution port 48c when viewed from vertically above the distribution port 48c, and a timing at which the first opening-closing portion 112a overlaps the distribution port 48c when viewed from vertically above the distribution port 48c is changed and set to a given value, as mentioned above, so that it is possible to manufacture a powder-containing article 2 in which the discrete article length L30 and the length L10 of the blank region are adequately set.

(5) Functions, Etc

As above, in the powder supply device 40 and the powder supply method in the above embodiment, the first opening-closing portion 112a and the second opening-closing portion 122a are rotationally driven such that they periodically overlap the distribution port 48c in the same cycle period, and the second opening-closing portion 122a closes the distribution port 48c at a timing later than that of the first opening-closing portion 112a. Further, the second opening-closing portion 122a is rotationally driven such that it extends from the rotation directional upstream-side edge 112a_2 of the first opening-closing portion 112a toward the upstream side of the rotation direction of the first opening-closing portions 112a, during a time period during which the rotational directional upstream-side edge 112a_2 of the first opening-closing portion 112a overlaps the distribution port 48c, when viewed from vertically above the distribution port 48c.

Further, a timing at which the first opening-closing portion 112a overlaps the distribution port 48c and a timing at which the second opening-closing portion 122a overlaps the distribution port 48c is changed to an adequate value by the control unit 49.

Thus, in the above embodiment, it is possible to change the length L10 of the blank region X1, independently of the length of the region X3 as the sum of the blank region X1 and the holding region X2, i.e., the discrete article length L30, which is determined by the cycle period of each of the first opening-closing portion 112a and the second opening-closing portion 122a, i.e., change these lengths L10, L30 to adequate values, respectively.

Further, the length L10 of the blank region X1 can be easily changed without largely varying the rotational speed of each of the first opening-closing portion 112a and the second opening-closing portion 122a during one cycle period, so that it is possible to keep down a load to be imposed on the motors 117, 127.

Further, by using the manufacturing apparatus 1 comprising the powder supply device 40, or by implementing the powder-containing article manufacturing method using the powder supply method, it is possible to manufacture a powder-containing article 2 in which the discrete article length L3 and the length L10 of the blank region X1 are adequately set.

In the above embodiment, the second opening-closing portion 122a closes the distribution port 48c at a position below the first opening-closing portion 112a.

Thus, part of the powder S which has not been able to be restricted from dropping toward the distribution port 48c by the first opening-closing portion 112a can be reliably received and restricted from dropping toward the distribution port 48c by the second opening-closing portion 122a.

In the above embodiment, the distribution port 48c is formed in a rectangular shape extending in a direction parallel to the width direction of the first sheet 201, and the first opening-closing portion 112a and the second opening-closing portion 122a are rotationally driven such that they overlap the distribution port 48c in a posture where the movement directional downstream-side edge 112a_1 of the first opening-closing portion 112a and the movement directional upstream-side edge 122a_2 of the second opening-closing portion 122a extend in the width direction of the first sheet 201.

Thus, the border between the holding region X2 and the blank region X1 in the first sheet 201 can be formed as a line extending in a direction orthogonal to the conveyance direction of the first sheet 201. Therefore, it is possible to accurately cut the powder-containing article 2 in the blank region X1 along the width direction, even when the length L10 of the blank region X1 of the powder-containing article 2 is relatively short.

(6) Second Embodiment

Although the first embodiment has been described based on an example in which each of the first opening-closing portion 112a and the second opening-closing portion 122a is rotated about an axis perpendicular to the bottom wall of the housing 48a, a specific structure of the mechanism 48 is not limited thereto, as long as the first opening-closing portion and the second opening-closing portion are capable of periodically opening the distribution port 48c.

Figure 12:
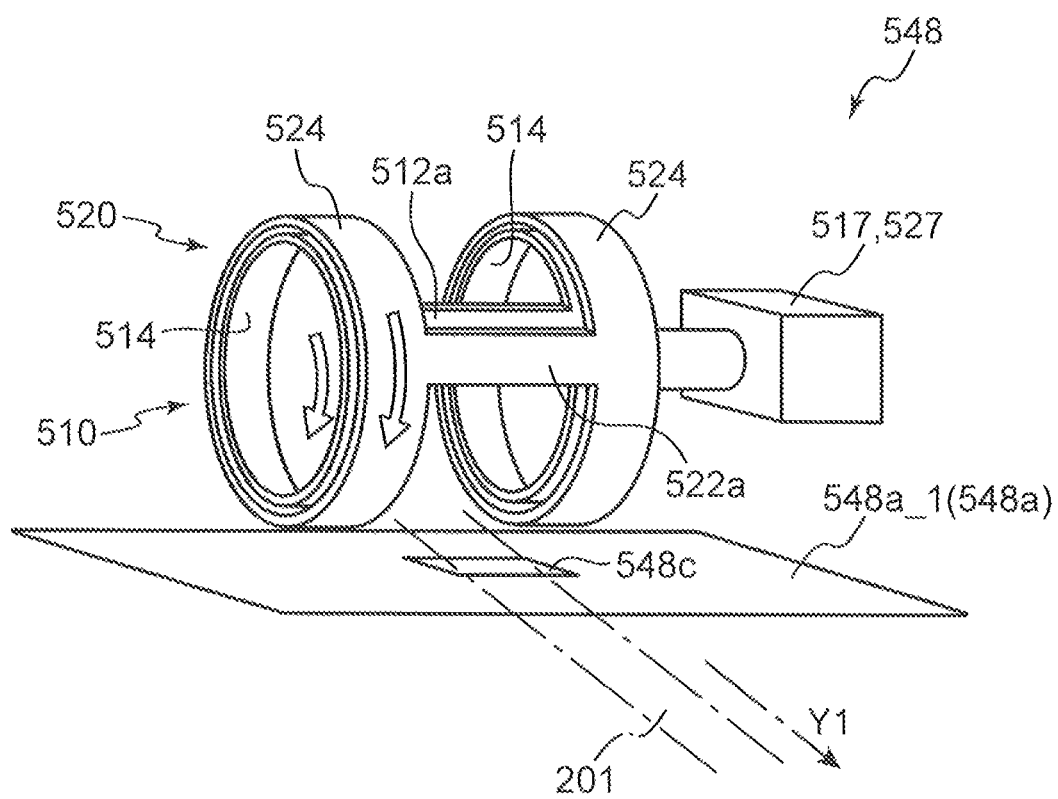
FIG. 12 is a diagram depicting a shutter unit in a powder-containing article manufacturing apparatus according to a second embodiment of the present invention.
Figure 13:
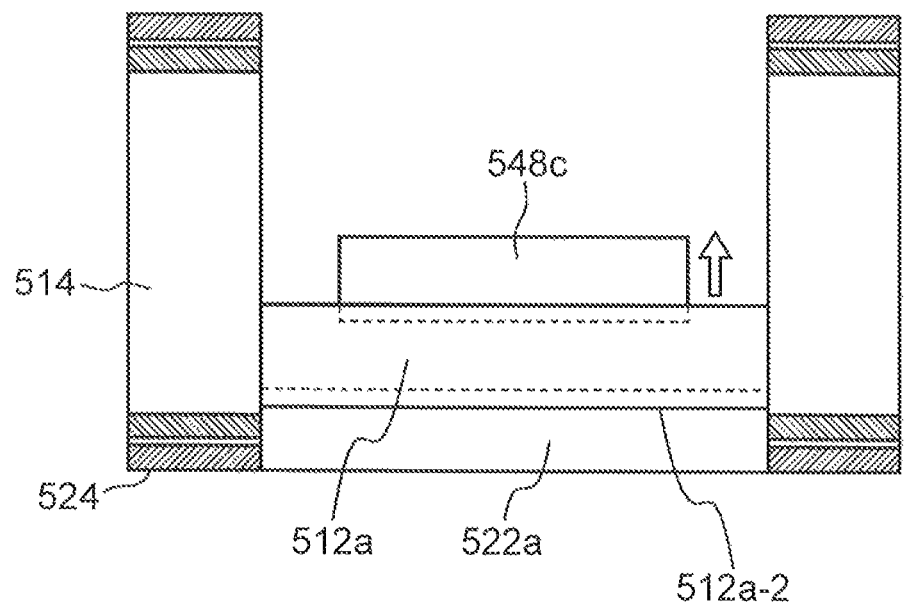
FIG. 13 is a diagram depicting a state at a time when a first opening-closing portion of the shutter unit depicted in FIG. 12 passes through above the distribution port.
Figure 14:
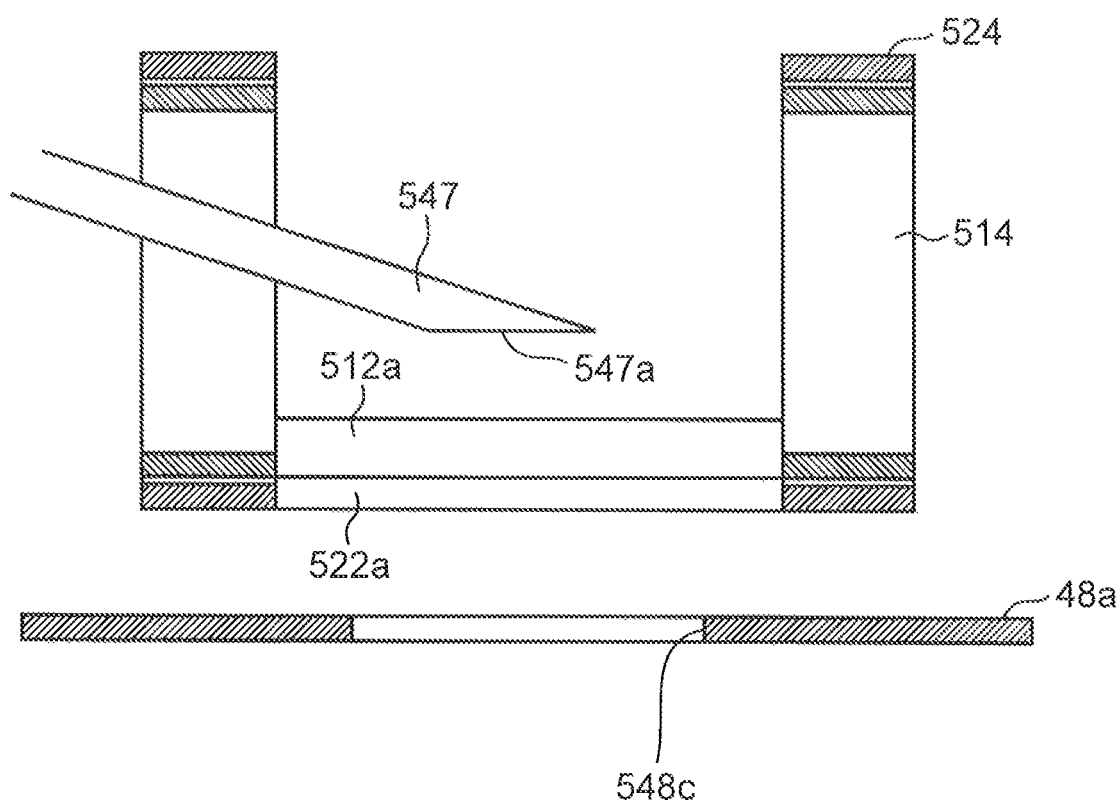
FIG. 14 is a diagram depicting a powder supply section in the second embodiment.

For example, in place of the above structure, a mechanism 548 depicted in FIGS. 12, 13 and 14, in a powder-containing article manufacturing apparatus according to a second embodiment of the present invention.

As depicted in FIG. 12, the mechanism 548 in the second embodiment comprises a first shutter unit 510 and a second shutter unit 520 each provided inside a housing 48a. However, in this mechanism 548, each of an aftermentioned first opening-closing portion 512a of the first shutter unit 510 and an aftermentioned second opening-closing portion 522a of the second shutter unit 520 is rotated about an axis extending parallel to a bottom wall 548a_1 of the housing 548a formed with a distribution port 48c.

Specifically, the first shutter unit 510 has a pair of hollow cylindrical-shaped support portions 514, 514 having a central axis extending in a direction parallel to the width direction of the first sheet 201. These support portions 514, 514 are disposed at positions spaced apart from each other in a direction parallel to the width direction of the first sheet 201. The support portions 514, 514 are coupled together by a first opening-closing portion 512a extending between the support portions 514, 514. The support portions 514, 514 and the first opening-closing portion 512a are configured to be rotated about the central axis of the support portion 514, 514 by a motor 517. Along with this rotation, the first opening-closing portion 512a periodically passes through above the distribution port 548c to open and close the distribution port 548c, as depicted in FIG. 13.

The second shutter unit 520 has the same structure, i.e., has a pair of support portions 524, 524, and a second opening-closing portion 522a coupling the support portions 524 together. The second shutter unit 520 is rotationally driven by a motor 527, such that it periodically passes through above the distribution port 548c to open and close the distribution port 548c.

The support portions 524, 524 and the second opening-closing portion 522a of the second shutter unit 520 are located on a radially outward side of the support portions 514, 514 and the first opening-closing portion 512a of the first shutter unit 510.

The motors 517, 527 are configured to rotate the first shutter unit 510 and the second shutter unit 520, respectively, about the same axis, in the same direction and in the same cycle period. Further, in the second embodiment, a control unit 49 is operable to change respective phases of the motors 517, 527 and thus an amount of a difference between a timings at which the opening-closing portion 512a closes the distribution port 548c and a timings at which the opening-closing portion 522a closes the distribution port 548c, as with the first embodiment.

In the mechanism 548 in the second embodiment configured as above, the first opening-closing portion 512a and the second opening-closing portion 522a are set to have a phase difference therebetween, so that, during a time periods during which an upstream-side edge 512a_2 of the first opening-closing portion 512a lying on an upstream side of an rotational direction of the first opening-closing portion 512a overlaps the distribution port 548c, the second opening-closing portion 522a is rotated such that it extends from the upstream-side edge 512a_2 toward the upstream side of the rotational direction of the first opening-closing portion 512a. Further, by changing an amount of the phase difference, it is possible to easily change the length L10 of the blank region X1 and the discrete article length L30, respectively, to adequate values, independently.

In the second embodiment, a powder guide section 547 is extended to a position just above the distribution port 548c through a radially inward region of the support portions 514, 524 of the shutter units 510, 520, and disposed such that the opening-closing portions 512a, 522a are rotated around a powder supply port 547a formed at a lower end of the powder guide section 547, as depicted in FIG. 14.

(7) Third Embodiment

Figure 15:
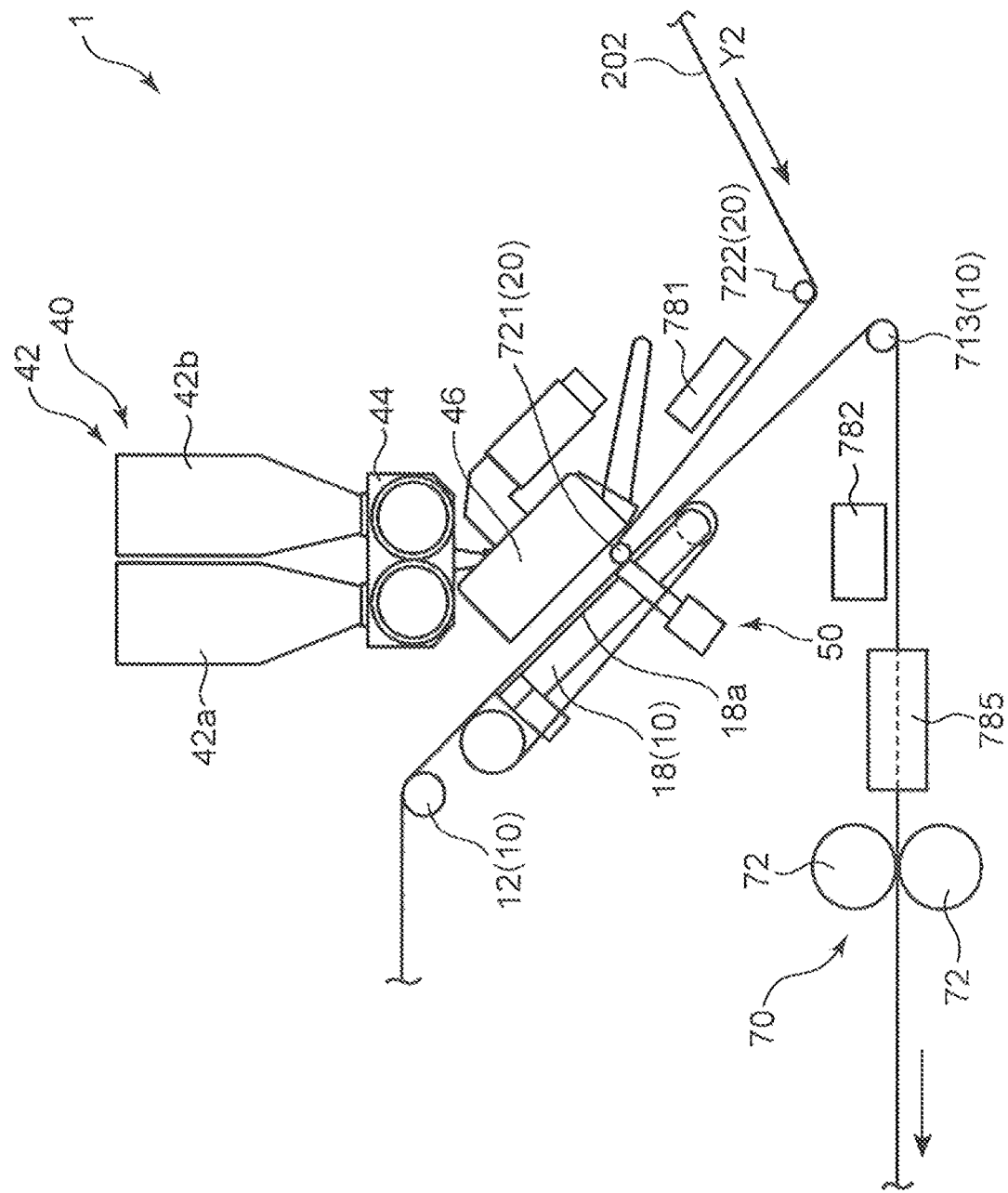
FIG. 15 is a diagram depicting a powder-containing article manufacturing apparatus according to a third embodiment of the present invention.
Figure 16:
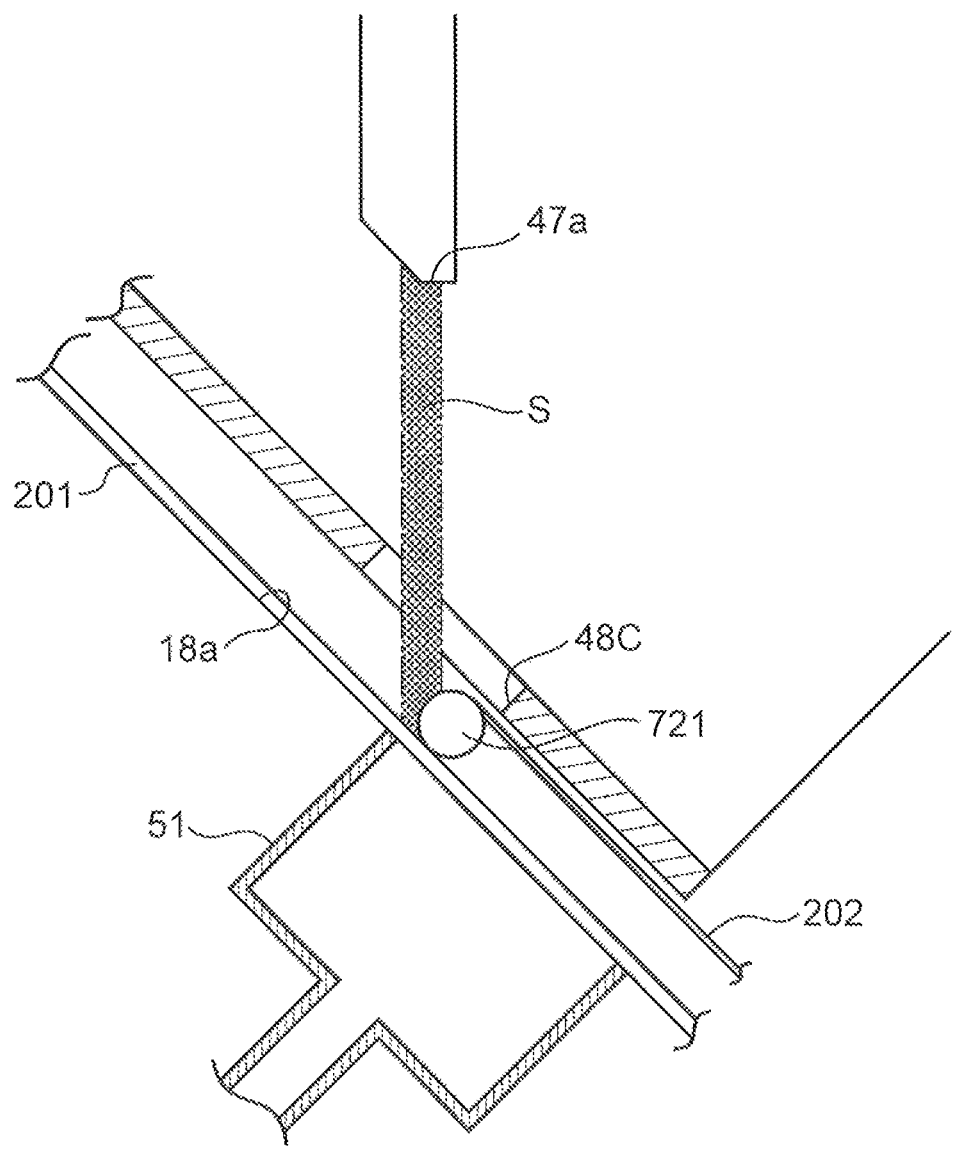
FIG. 16 is a diagram enlargedly depicting a part of FIG. 15.

The first embodiment has been described based on an example in which the guide roll 21 of the second sheet conveyance device 20 for supplying the second sheet 202 onto the obverse surface of the first sheet 201 is disposed downstream (in the conveyance direction Y1 of the first sheet 201) of the distribution port 48c, i.e., a portion from which the powder S is supplied to the first sheet S. Alternatively, it may be disposed as depicted in FIG. 15 and FIG. 16 enlargedly depicting a part of FIG. 15.

Specifically, in the third embodiment, one 721 of two guide rolls 721, 722 of a second sheet conveyance device 20 for supplying the second sheet 202 onto the obverse surface of the first sheet 201 is disposed at a position opposed to the distribution port 48c, i.e., a powder supply position where the powder S is supplied to the first sheet 201

More specifically, in the third embodiment, the first sheet 201 is conveyed obliquely downwardly, as with the first embodiment. Accordingly, a second sheet supply position where the guide roll 721 supplies the second sheet 202 to the obverse surface of the first sheet 201 is located slightly upstream, in the conveyance direction of the first sheet 201, of a position vertically below a shaft center of the guide roll 721, and an upper side, in the vertical direction, of the second sheet supply position is opened. The distribution port 48c is disposed to face a position upward, in the vertical direction, of the second sheet supply position position. Thus, in the third embodiment, the powder supply position where the powder S is supplied to the first sheet 201 and the second sheet supply position where the second sheet 202 is supplied to the first sheet 201 are coincident with each other, so that, at this position, the powder S is supplied to the first sheet 201, and simultaneously the second sheet 202 is supplied to the first sheet 201. Therefore, in the third embodiment, it is possible to more reliably suppress leakage of the powder S from between the two sheets 201, 202.

Further, in the third embodiment, as with the first embodiment, a first adhesive application device 781 is provided at a position upstream, in the conveyance direction of the second sheet 202, of the guide roll 721, so that, simultaneously with supply of the powder S to the first sheet 201, the first sheet 201 and the second sheet 202 are bonded together. This makes it possible to more reliably suppress the leakage of the powder S from between the two sheets 201, 202. In the third embodiment, the guide roll 721 is configured to pressure-join the first sheet 201 and the second sheet 202 in their thickness direction, in the same manner as that in the first embodiment.

In the third embodiment, a suction passage 51 extends toward the downstream side from a position just below the distribution port 48c, i.e., the powder supply position where the powder S is supplied to the first sheet 201, and applies suction to a region from the powder supply position to a position downstream of the powder supply position, in the same manner as that in the first embodiment.

In the third embodiment, a roller 713, a second adhesive application device 782, a folding device 785 and a pressure-joining device 70 are provided, and the second sheet 201 and the first sheet 202 are further bonded together and an assembly thereof is pressure-joined in a thickness direction thereof, in the same manner as that in the first embodiment.

(8) Modifications

In the first embodiment, each of the shutter plates 112, 122 is formed in an L shape. Alternatively, it may be formed in any other suitable shape. For example, it may be formed in an I shape having an opening-closing portion and a coupling portion extending from one end of the opening-closing portion in the rightward-leftward direction. In the first embodiment, each of the edges of the opening-closing portions 112a, 122a has a linear shape extending along a direction orthogonal to the conveyance direction of the first sheet 201. Alternatively, each of the edges may have any other suitable shape such as a wave shape, a chevron shape, or a concave shape. Further, each of the edges does not necessarily extend in a direction orthogonal to the conveyance direction of the first sheet, but may be a shape extending in a direction oblique to the conveyance direction.

The first embodiment has been described based on an example in which the first opening-closing portion 112a and the second opening-closing portion 122a have the same width. However, the widths of the two opening-closing portions may be different from each other. In this case, the length of the blank region can be changed by rotating only one of the opening-closing portions, as comparted to when only the other opening-closing portion is rotated.

In the first embodiment, the first opening-closing portion 112a and the second opening-closing portion 122a are rotationally moved, respectively, by the motor 117 and the motor 127. However, each of the two opening-closing portions may be configured to be reciprocatingly moved by a drive means (such as a motor) via a link mechanism.

A drive means (such as a motor) for rotating each of the shutter plates is not necessarily configured to rotate the shutter plate at a constant speed, but may be configured to vary the rotational speed during one cycle period, to the extent that an excessive load is not imposed on the motor. That is, for example in the first embodiment, the rotational speed of each of the first opening-closing portion 112a and the second opening-closing portion 122a may be varied during one cycle period to the extent that an excessive load is not imposed on the motor, while changing the amount of the difference between the overlapping timing of the first opening-closing portion 112a with the distribution port 48c and the overlapping timing of the second opening-closing portion 122a with the distribution port 48c. Specifically, a speed at which each of the first opening-closing portion 112a and the second opening-closing portion 122a passes through above the distribution port 48c and a speed during the remaining rotation movement in one cycle period are set to become different from each other. This makes it possible to change and set the length L10 of the blank region 10 with respect to the discrete article length L30, in a wider range.

As used here, the term "cycle period" means a time interval between adjacent timings at each of which each of the opening-closing portions passes through above the distribution port. Thus, in the case where each of the opening-closing portions is rotationally moved to pass through above the distribution port once per 360-rotation, as in the first embodiment, the term "one cycle period" means a time period during which each of the opening-closing portions is rotated 360 degrees. On the other hand, in the case where each of the opening-closing portions is reciprocatingly moved to pass through above the distribution port once per stroke, the term "one cycle period" means a time interval between a timing at which, during a forward movement in a stroke, each of the opening-closing portions passes through above the distribution port and a timing at which, during a backward movement in the stroke, each of the opening-closing portions passes through above the distribution port.

In the first embodiment, the movement direction of each of the opening-closing portions 112a, 122a at a position just above the distribution port 48c is set to be the same as the conveyance direction of the first sheet 201. However, the movement direction of each of the opening-closing portions 112a, 122a may be opposite to the conveyance direction of the first sheet 201. Further, the movement direction of each of the opening-closing portions 112a, 122a does not have to be parallel to the conveyance direction of the first sheet 201, but may be set to any other suitable direction. For example, when the first sheet is conveyed obliquely downwardly, each of the opening-closing portions 112a, 122a may be moved in a horizontal direction.

The first embodiment has been described based on an example in which the control unit 49 operates to set and change the rotation start timings of the motors 117, 127 to thereby set and change the amount of the difference between the overlapping timings of the opening-closing portions 112a, 122a with the distribution port 48c. However, the amount of the difference between the overlapping timings of the opening-closing portions 112a, 122a with the distribution port 48c may be set and changed by controlling respective rotations of the motors 117, 127 through an arbitrary method.

As the powder S, one type of SAP powder having a single absorption property may be used, or a mixture of one type of SAP powder having a high liquid-absorbability and another type of SAP powder having a high absorption rate may be used. For example, it is conceivable that the type of SAP powder having a high liquid-absorbability and the type of SAP powder having a high absorption rate are stored, respectively, in the tank 42a and the tank 42b of the powder storage unit 42 depicted in FIG. 1, and the two type of SAP powders are fed from the two tanks 42a, 42b at a given ratio. The powder S may be any liquid-absorbable powder other than the SAP powders. Further, the powder S is not limited to a liquid-absorbable powder. For example, as the powder S, a powder of cool sensation material or fragrance material may be used. Further, the plural types of powders may be used in combination.

A specific configuration of the first sheet 201 is not limited to the aforementioned configuration.

For example, as the first sheet 201, a sheet may be used which is formed with a plurality of storing portions each depressed downwardly to store therein a powder, as disclosed in the WO 2014/104118A. Further, the first sheet 201 may be a sheet including a bulky non-woven fabric layer, or may be a sheet composed of a plurality of layers.

The second sheet 202 is not limited to a tissue paper. For example, it may be comprised of a non-woven fabric.

Although the above embodiments have been described based on an example in which the distribution port 48c is located adjacent to the first sheet 201, the distribution port 48c may be disposed at a position spaced apart upwardly from the first sheet 201. In this case, a passage or the like for guiding the powder S from the distribution port 48c toward the first sheet 201 may be formed.

Although the above embodiments have been described based on an example in which the first sheet 201 is conveyed obliquely downwardly at a position below the distribution port 48c, the conveyance direction of the first sheet 201 is not limited thereto. For example, the first sheet 201 may be conveyed horizontally or obliquely upwardly at a position below the distribution port 48c.

Although the above embodiments have been described based on an example in which the assembly of the first sheet 201 and the second sheet 202 is press-joined by using the rollers 72, 72, a procedure and a device for press-joining the assembly of the sheets 201, 202 are not limited thereto. Further, for example, in the case where the guide roll 21 or the guide roll 721 functioning as the second sheet supply section is capable of sufficiently press-joining the two sheets 201, 202, the pressure-joining device 70 may be omitted.

Although the above embodiments have been described based on an example in which a hot-melt adhesive is used for bonding between the two sheets 201, 202, a specific configuration for bonding the two sheets 201, 202 together is not limited thereto. For example, the two sheets 201, 202 may be bonded together by means of heat-sealing or ultrasonic bonding.

Although the above embodiments have been described based on an example in which the metering unit 44 feeds the powder S downwardly at a given flow rate, this flow rate may be constant or may be temporally changed. For example, in the case where it is necessary to place a larger amount of the powder S in a given zone of the first sheet in the conveyance direction Y1 of the first sheet 201, the flow rate may be increased at a timing corresponding to the given zone.

Further, a specific configuration of the metering unit 44 is not limited to the aforementioned configuration.

Although the above embodiments have been described based on an example in which the powder S is uniformly supplied in the width direction of the first sheet 201, a supply amount of the powder S to the first sheet 201 may be changed in the width direction of the first sheet 201.

For example, the powder guide section 47 may be divided, in the width direction of the first sheet 201, into a plurality of discrete passages, such that the powder S falls downwardly through respective ones of the discrete passages. Further, at least part of the powder S passing through some of the discrete passages may be appropriately removed from the some passages by removing means (mechanical means, blow means using airflow, or suction means) to change the supply amount of the powder S to the first sheet 201 in the width direction of the first sheet 201. Specifically, it is conceivable that the shape of the holding region is formed in a so-called hourglass-like shape in which the width of an intermediate portion of the first sheet 201 in its longitudinal direction is narrower than the remaining portion. It is also conceivable that no powder is supplied to an intermediate portion of the first sheet 201 in its width direction, to form a pattern in which two lines of holding regions are arranged in spaced-apart relation in the width direction of the first sheet 201. Further, it is conceivable that three or more lines of holding regions are arranged in spaced-apart relation to each other in the width direction of the first sheet 201.

Although the first embodiment has been described based on an example in which the belt conveyer 18 is used as a device for conveying the first sheet 201 to the powder distribution unit 46, a conveyance drum may be used in place of the belt conveyer 18. By using the conveyance drum in this manner, a device size in the conveyance direction of the first sheet 201, and a device installation area can be reduced as compared to the belt conveyer 18. On the other hand, the belt conveyer 18 makes it possible to avoid a situation where centrifugal force is applied to the first sheet 201 and the powder S, differently from the case using the conveyance drum, and thus more efficiently supply the powder S to the first sheet 201.

The above specific embodiments mainly include inventions having the following features.

The present invention provides a powder supply method for supplying a powder to a sheet being conveyed along a conveyance path. The powder supply method implements: a distribution step of dropping the powder from a storage section storing therein the powder, to distribute the powder onto a surface of the sheet through a distribution port; a first closing step of moving a first opening-closing portion such that the first opening-closing portion periodically overlaps the distribution port when viewed from vertically above the distribution port, to periodically close the distribution port by the first opening-closing portion; a second closing step of moving a second opening-closing portion such that the second opening-closing portion overlaps the distribution port when viewed from vertically above the distribution port, in a same cycle period as that of the first opening-closing portion and at a timing later than that of the first opening-closing portion, to periodically close the distribution port by the second opening-closing portion, and moving the second opening-closing portion such that the second opening-closing portion extends from an upstream-side edge of the first opening-closing portion lying on an upstream side of a movement direction of the first opening-closing portion toward the upstream side of the movement direction of the first opening-closing portion, during a time period during which the upstream-side edge of the first opening-closing portion overlaps the distribution port, when viewed from vertically above the distribution port; and a timing setting step of setting a difference between a timing at which the second opening-closing portion overlaps the distribution port when viewed from vertically above the distribution port, and a timing at which the first opening-closing portion overlaps the distribution port when viewed from vertically above the distribution port.

In the present invention, the "timing at which the opening-closing portion overlaps the distribution port" means a beginning or an end of a time period during which the opening-closing portion overlaps the distribution port. More specifically, the beginning is a timing at which the downstream-side edge of the opening-closing portion lying on a downstream side of the movement direction of the opening-closing portion overlaps the upstream-side opening edge of the distribution port lying on an upstream side of the movement direction of the opening-closing portion, and the end is a timing at which the upstream-side edge of the opening-closing portion lying on the upstream side of the movement direction of the opening-closing portion overlaps the downstream-side opening edge of the distribution port lying on the downstream side of the movement direction of the opening-closing portion. The "timing at which the opening-closing portion overlaps the distribution port (overlapping timing of the opening-closing portion with the distribution port)" is one of them. Further, the "difference" in the overlapping timing means a temporal difference (time lag) between respective overlapping timings of the downstream-side edges of the first and second opening-closing portion with the upstream-side opening edge of the distribution port, or between respective overlapping timings of the upstream-side edges of the first and second opening-closing portion with the downstream-side opening edge of the distribution port, on the basis of the movement direction of each of the first and second opening-closing portion.

In the powder supply method of the present invention, it is possible to continuously close the distribution port by the first opening-closing portion and the second opening-closing portion, and set and change the difference between the timing at which the second opening-closing portion overlaps the distribution port and the timing at which the first opening-closing portion overlaps the distribution port, and thus a time period during which the distribution port is continuously closed by the first opening-closing portion and the second opening-closing portion. Therefore, by setting and changing this time period to an adequate value, and setting and changing the cycle period of each of the first and second opening-closing portion to an adequate value, it is possible to easily set and change the length of a holding region (region of the sheet holding the powder supplied thereto) and the length of a blank region (region of the sheet having no powder) to adequate values, respectively. In particular, the length of the blank region can be appropriately changed without largely varying the movement speed of each of the first and second opening-closing portion during one cycle period, so that it is possible to keep down a load to be imposed on a drive unit for driving each of the first and second opening-closing portion.

In the powder supply method of the present invention, although the movement of the opening-closing portion may be a reciprocating movement, it is preferable to employ a rotational movement from a viewpoint of its capability of more smoothly moving the opening-closing portion.

Preferably, in the powder supply method of the present invention, the second closing step includes moving the second opening-closing portion such that the second opening-closing portion overlaps the distribution port at a position below the first opening-closing portion.

According to this feature, part of the powder which has not been able to be restricted from dropping toward the distribution port by the first opening-closing portion can be received by the following second opening-closing portion, so that it is possible to reliably suppress a situation where part of the powder is supplied to the sheet through the distribution port during a time period during which the first opening-closing portion and the second opening-closing portion close the distribution port.

Preferably, in the powder supply method of the present invention, the distribution port has a shape in which each of an upstream-side opening edge lying on an upstream side of a conveyance direction of the sheet, and a downstream-side opening edge lying on a downstream side of the conveyance direction of the sheet, extends in a direction orthogonal to the conveyance direction of the sheet, wherein: the first closing step includes moving the first opening-closing portion such that it passes through above the distribution port, in a posture where a downstream-side edge of the first opening-closing portion lying on a downstream side of the movement direction of the first opening-closing portion extends in the direction orthogonal to the conveyance direction of the sheet when viewed from vertically above the distribution port; and the second closing step includes moving the second opening-closing portion such that it passes through above the distribution port, in a posture where an upstream-side edge of the second opening-closing portion lying on an upstream side of a movement direction of the second opening-closing portion extends in the direction orthogonal to the conveyance direction of the sheet when viewed from vertically above the distribution port.

Thus, the border between the holding region and the blank region can be formed as a line extending in a direction orthogonal to the conveyance direction of the sheet.

The present invention further provides a method for manufacturing a powder-containing article containing a powder, by using the above powder supply method. This method implements: the timing setting step; a conveyance step of conveying the sheet along the conveyance path; a powder supply step of supplying the powder onto a surface of the sheet being conveyed along the conveyance path; a second sheet supply step of supplying a second sheet onto the surface of the sheet being conveyed along the conveyance path, at a powder supply position where the powder is supplied to the sheet or at a position downstream of the powder supply position in the conveyance direction of the sheet; and a bonding step of bonding the sheet and the second sheet supplied onto the surface of the sheet, together, wherein the powder supply step includes implementing the distribution step, the first closing step, and the second closing step.

In this manufacturing method of the present invention, it is possible to easily change the length of the holding region holding the powder supplied thereto between the first sheet and the second sheet, and the length of the blank region having no powder, respectively, to adequate values, independently, while suppressing a situation where an excessive load is imposed on the drive unit for driving each of the first and second opening-closing portion.

The present invention further provides a powder supply device for supplying a powder to a sheet being conveyed along a conveyance path. The powder supply device comprises: a storage section storing therein the powder; a distribution port which allows the powder falling from the storage section to pass therethrough toward an obverse side of the sheet; a first opening-closing portion and a second opening-closing portion each having a shape capable of closing the distribution port when viewed from vertically above the distribution port; a first drive device which drives the first opening-closing portion; a second drive device which drives the second opening-closing portion; and a control device which controls the first drive device and the second drive device, wherein: the first drive device moves the first opening-closing portion such that the first opening-closing portion periodically overlaps the distribution port when viewed from vertically above the distribution port; the second drive device moves the second opening-closing portion such that the second opening-closing portion overlaps the distribution port when viewed from vertically above the distribution port, in a same cycle period as that of the first opening-closing portion and at a timing later than that of the first opening-closing portion, and extends from an upstream-side edge of the first opening-closing portion lying on an upstream side of a movement direction of the first opening-closing portion toward the upstream side of the movement direction of the first opening-closing portion, during a time period during which the upstream-side edge of the first opening-closing portion overlaps the distribution port, when viewed from vertically above the distribution port; and the control device is capable of changing a difference between a timing at which the second opening-closing portion overlaps the distribution port when viewed from vertically above the distribution port, and a timing at which the first opening-closing portion overlaps the distribution port when viewed from vertically above the distribution port.

In the powder supply device of the present invention, it is possible to continuously close the distribution port by the first opening-closing portion and the second opening-closing portion, and set and change the difference between the timing at which the second opening-closing portion overlaps the distribution port and the timing at which the first opening-closing portion overlaps the distribution port, and thus a time period during which the distribution port is continuously closed by the first opening-closing portion and the second opening-closing portion. Therefore, by setting and changing this time period to an adequate value, and setting and changing the cycle period of each of the first and second opening-closing portion to an adequate value, it is possible to set and change the length of the holding region and the length of the blank region to adequate values, respectively. This makes it possible to easily change the lengths of these regions, respectively, to adequate values, while suppressing a situation where an excessive load is imposed on the drive unit for driving each of the first and second opening-closing portion.

Preferably in the powder supply device of the present invention, the second drive device moves the second opening-closing portion such that the second drive device overlaps the distribution port at a position below the first opening-closing portion.

According to this feature, part of the powder which has not been able to be restricted from dropping toward the distribution port by the first opening-closing portion can be received by the following second opening-closing portion, so that it is possible to reliably suppress a situation where part of the powder is supplied to the sheet through the distribution port during a time period during which the first opening-closing portion and the second opening-closing portion close the distribution port.

Preferably, in the powder supply device of the present invention, the distribution port has a shape in which each of an upstream-side opening edge lying on an upstream side of a conveyance direction of the sheet, and a downstream-side opening edge lying on a downstream side of the conveyance direction of the sheet, extends in a direction orthogonal to the conveyance direction of the sheet, and wherein: the first drive device moves the first opening-closing portion such that the first opening-closing portion passes through above the distribution port, in a posture where a downstream-side edge of the first opening-closing portion lying on a downstream side of the movement direction of the first opening-closing portion extends in the direction orthogonal to the conveyance direction of the sheet; and the second drive device moves the second opening-closing portion such that the second opening-closing portion passes through above the distribution port, in a posture where an upstream-side edge of the second opening-closing portion lying on an upstream side of a movement direction of the second opening-closing portion extends in the direction orthogonal to the conveyance direction of the sheet.

According to this feature, the border between the holding region and the blank region can be formed as a line extending in a direction orthogonal to the conveyance direction of the sheet.

The present invention further provides an apparatus for manufacturing a powder-containing article containing a powder. This apparatus comprises: the above powder supply device; a sheet conveyance device which conveys the sheet along the conveyance path; a second sheet supply section which supplies a second sheet onto a surface of the sheet, at a powder supply position of the conveyance path where the powder is supplied to the sheet or at a position downstream of the powder supply position in a conveyance direction of the sheet; and a bonding device which is provided on the conveyance path, and bonds the sheet and the second sheet together, at a second sheet supply position where the second sheet is supplies from the second sheet supply section onto the surface of the sheet, or at a position downstream of the second sheet supply position in the conveyance direction of the sheet.

In this manufacturing apparatus of the present invention, it is possible to easily change the length of the holding region holding the powder supplied thereto between the first sheet and the second sheet, and the length of the blank region having no powder, respectively, to adequate values, independently, while suppressing a situation where an excessive load is imposed on the drive unit for driving each of the first and second opening-closing portion.

LIST OF REFERENCE SIGNS

1: powder-containing article manufacturing apparatus
40: powder supply device
47a: powder supply port
48c: distribution port
112a: first opening-closing portion (first embodiment)
122a: second opening-closing portion (first embodiment)
201: first sheet
512a: first opening-closing portion (second embodiment)
522a: second opening-closing portion (second embodiment)
S: powder

The invention claimed is:

1. A powder supply method for supplying a powder to a sheet being conveyed along a conveyance path, the powder supply method comprising:
dropping the powder from a storage section storing therein the powder, to distribute the powder onto a surface of the sheet through a distribution port;
moving a first opening-closing portion such that the first opening-closing portion periodically overlaps the distribution port when viewed from vertically above the distribution port, to periodically close the distribution port by the first opening-closing portion;
moving a second opening-closing portion such that the second opening-closing portion overlaps the distribution port when viewed from vertically above the distribution port, in a same cycle period as that of the first opening-closing portion and at a timing later than that of the first opening-closing portion, to periodically close the distribution port by the second opening-closing portion, and moving the second opening-closing portion such that the second opening-closing portion extends from an upstream-side edge of the first opening-closing portion lying on an upstream side of a movement direction of the first opening-closing portion toward the upstream side of the movement direction of the first opening-closing portion, during a time period during which the upstream-side edge of the first opening-closing portion overlaps the distribution port, when viewed from vertically above the distribution port; and
setting a difference between a timing at which the second opening-closing portion overlaps the distribution port when viewed from vertically above the distribution port, and a timing at which the first opening-closing portion overlaps the distribution port when viewed from vertically above the distribution port.

2. The powder supply method according to claim 1, wherein the moving the second opening-closing portion is performed such that the second opening-closing portion overlaps the distribution port at a position below the first opening-closing portion.

3. The powder supply method according to claim 1, wherein the distribution port has a shape in which each of an upstream-side opening edge lying on an upstream side of a conveyance direction of the sheet, and a downstream-side opening edge lying on a downstream side of the conveyance direction of the sheet, extends in a direction orthogonal to the conveyance direction of the sheet,
wherein the moving the first opening-closing portion is performed such that the first opening-closing portion passes through above the distribution port, in a posture where a downstream-side edge of the first opening-closing portion lying on a downstream side of the movement direction of the first opening-closing portion extends in the direction orthogonal to the conveyance direction of the sheet when viewed from vertically above the distribution port; and
wherein the moving the second opening-closing portion is performed such that the second opening-closing portion passes through above the distribution port, in a posture where an upstream-side edge of the second opening-closing portion lying on an upstream side of a movement direction of the second opening-closing portion extends in the direction orthogonal to the conveyance direction of the sheet when viewed from vertically above the distribution port.

4. A method for manufacturing a powder-containing article containing a powder, by using the powder supply method according to claim 1, wherein the sheet is a first sheet the method comprising:

conveying the first sheet along the conveyance path;

supplying the powder onto a surface of the first sheet being conveyed along the conveyance path;

supplying a second sheet onto the surface of the first sheet being conveyed along the conveyance path, at a powder supply position where the powder is supplied to the first sheet or at a position downstream of the powder supply position in the conveyance direction of the first sheet; and bonding the first sheet and the second sheet supplied onto the surface of the first sheet, together, wherein the supplying the powder onto the surface of the first sheet being conveyed along the conveyance path includes the dropping of the powder from a storage section, the moving of the first opening-closing portion such that the first opening-closing portion periodically overlaps the distribution port, and the moving of the second opening-closing portion such that the second opening-closing portion overlaps the distribution port.

5. A powder supply device for supplying a powder to a sheet being conveyed along a conveyance path, the powder supply device comprising: a storage section storing therein the powder; a distribution port which allows the powder falling from the storage section to pass therethrough toward an obverse side of the sheet; a first opening-closing portion and a second opening-closing portion each having a shape for closing the distribution port when viewed from vertically above the distribution port; a first drive device which drives the first opening-closing portion; a second drive device which drives the second opening-closing portion; and a control device which controls the first drive device and the second drive device;

wherein the first drive device is configured to move the first opening-closing portion such that the first opening-closing portion periodically overlaps the distribution port when viewed from vertically above the distribution port;

wherein the second drive device is configured to move the second opening-closing portion such that the second opening-closing portion overlaps the distribution port when viewed from vertically above the distribution port, in a same cycle period as that of the first opening-closing portion and at a timing later than that of the first opening-closing portion, and extends from an upstream-side edge of the first opening-closing portion lying on an upstream side of a movement direction of the first opening-closing portion toward the upstream side of the movement direction of the first opening-closing portion, during a time period during which the upstream-side edge of the first opening-closing portion overlaps the distribution port, when viewed from vertically above the distribution port; and wherein the control device is configured to change a difference between a timing at which the second opening-closing portion overlaps the distribution port when viewed from vertically above the distribution port, and a timing at which the first opening-closing portion overlaps the distribution port when viewed from vertically above the distribution port.

6. The powder supply device according to claim 5, wherein the second drive device moves the second opening-closing portion such that the second opening-closing portion overlaps the distribution port at a position below the first opening-closing portion.

7. The powder supply device according to claim 5, wherein the distribution port has a shape in which each of an upstream-side opening edge lying on an upstream side of a conveyance direction of the sheet, and a downstream-side opening edge lying on a downstream side of the conveyance direction of the sheet, extends in a direction orthogonal to the conveyance direction of the sheet;

wherein the first drive device is configured to move the first opening-closing portion such that the first opening-closing portion passes through above the distribution port, in a posture where a downstream-side edge of the first opening-closing portion lying on a downstream side of the movement direction of the first opening-closing portion extends in the direction orthogonal to the conveyance direction of the sheet; and wherein the second drive device moves the second opening-closing portion such that the second opening-closing portion passes through above the distribution port, in a posture where an upstream-side edge of the second opening-closing portion lying on an upstream side of a movement direction of the second opening-closing portion extends in the direction orthogonal to the conveyance direction of the sheet.

8. An apparatus for manufacturing a powder-containing article containing a powder, comprising:

the powder supply device according to claim 5, wherein the sheet is a first sheet;

a sheet conveyance device configured to convey the first sheet along the conveyance path;

a second sheet supply section configured to supply a second sheet onto a surface of the first sheet, at a powder supply position of the conveyance path where the powder is supplied to the first sheet or at a position downstream of the powder supply position in a conveyance direction of the sheet; and a bonding device which is provided on the conveyance path, and bonds the sheet and the second sheet together, at a second sheet supply position where the second sheet is supplied from the second sheet supply section onto the surface of the first sheet, or at a position downstream of the second sheet supply position in the conveyance direction of the first sheet.

* * * * *